US009132185B2

(12) United States Patent
Ni et al.

(10) Patent No.: US 9,132,185 B2
(45) Date of Patent: Sep. 15, 2015

(54) MODIFIED LIVE-ATTENUATED VACCINES (MLV) CREATED BY DNA SHUFFLING AGAINST PORCINE REPRODUCTIVE AND RESPIRATORY SYNDROME VIRUS (PRRSV)

(75) Inventors: Yanyan Ni, Blacksburg, VA (US); Yaowei Huang, Blacksburg, VA (US); Xiang-Jin Meng, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 59 days.

(21) Appl. No.: 13/701,729

(22) PCT Filed: Jun. 2, 2011

(86) PCT No.: PCT/US2011/038930
§ 371 (c)(1),
(2), (4) Date: Feb. 15, 2013

(87) PCT Pub. No.: WO2011/153351
PCT Pub. Date: Dec. 8, 2011

(65) Prior Publication Data
US 2013/0142824 A1    Jun. 6, 2013

Related U.S. Application Data

(60) Provisional application No. 61/350,685, filed on Jun. 2, 2010.

(51) Int. Cl.
*A61K 39/12* (2006.01)
*C12N 7/00* (2006.01)
*A61K 39/00* (2006.01)

(52) U.S. Cl.
CPC . *A61K 39/12* (2013.01); *C12N 7/00* (2013.01); *A61K 2039/5254* (2013.01); *A61K 2039/552* (2013.01); *C12N 2770/10034* (2013.01); *C12N 2770/10052* (2013.01)

(58) Field of Classification Search
None
See application file for complete search history.

(56) References Cited

U.S. PATENT DOCUMENTS

| | | | |
|---|---|---|---|
| 7,666,585 | B2 | 2/2010 | Zhang et al. |
| 2003/0086945 | A1 | 5/2003 | Collins et al. |
| 2006/0240041 | A1 | 10/2006 | Meulenberg et al. |
| 2007/0269445 | A1* | 11/2007 | Paul et al. .................. 424/159.1 |
| 2008/0311143 | A1 | 12/2008 | Zhang et al. |
| 2010/0068225 | A1* | 3/2010 | Tian ........................... 424/204.1 |
| 2013/0142824 | A1* | 6/2013 | Ni et al. ...................... 424/205.1 |

FOREIGN PATENT DOCUMENTS

| | | | |
|---|---|---|---|
| CN | 101603035 | * | 12/2009 |
| WO | WO-98 50426 A1 | | 11/1998 |
| WO | WO-01 00234 A2 | | 1/2001 |
| WO | WO 2008/134697 A2 | | 11/2008 |

OTHER PUBLICATIONS

Proquest English translation of Yibao et al. (CN 101603035, Dec. 16, 2009).*
Baron et al. Annales de recherches vétérinaires. 1992; 23 (2): 161-166).*
Li et al. (Veterinary Microbiology. 2009; 138: 150-155).*
Abrahamson, Dale R., et al; Intestinal Absorption of Immune Complexes by Neonatal Rats: A Route of Antigen Transfer from Mother to Young; Science; (Nov. 2, 1979); pp. 567-569; vol. 206; No. 4418; American Association for the Advancement of Science.
Allende, R., et al.; North American and European Porcine Reproductive and Respiratory Syndrome Viruses Differ in Non-Structural Protein Coding Regions; Journal of General Virology; (1999); pp. 307-315; vol. 80.
Ansari, Israrul H., et al; Influence of N-Linked Glycosylation of Porcine Reproductive and Respiratory Syndrome Virus GP5 on Virus Infectivity, Antigenicity, and Ability to Induce Neutralizing Antibodies; Journal of Virology; (Apr. 2006); pp. 3994-4004; vol. 80; No. 8; American Society for Microbiology.
Apt, Doris, et al.; Tetravalent Neutralizing Antibody Response Against Four Dengue Serotypes by a Single Chimeric Dengue Envelope Antigen; Vaccine; (2006); pp. 335-344; vol. 24; Elsevier.
Balasuriya, Undeni B.R., et al; Characterization of the Neutrilization Determinants of Equine Arteritis Virus Using Recombinant Chimeric Viruses and Site-Specific Mutagenesis of an Infectious cDND Clone; Viorolgy; (2004); pp. 235-346; vol. 321; Elsevier Inc.
Bastos, Reginaldo G., et al; Immune Response of Pigs Inoculated with *Mycobacterium bovis* BCG Expressing a Truncated Form of GP5 and M Protein of Porcine Reproductive and Respiratory Syndrome Virus; Vaccine: (2004); pp. 467-474; vol. 22; Elsevier.
Bautisa, E. M., et al; Structural Polypeptides of the American (VR-2332) Strain of Porcine Reproductive and Respiratory Syndrome Virus; Archives of Virology; (1996); pp. 1357-1365; vol. 141; Springer-Verlag.
Brideeau-Andersen, Amy D., et al; Directed Evolution of Gene-Shuffled IFN-α Molecules with Activity Profiles Tailored for Treatment of Chronic Viral Diseases; PNAS; (May 15, 2007); pp. 8269-8274; vol. 104; No. 20.
Burgers, Wendy A., et al; Design and Preclinical Evaluation of a Multigene Human immunodeficiency Virus Type 1 Subtype C DNA Vaccine for Clinical Trial; Journal of General Virology; (2006); pp. 399-410; vol. 87; SGM.

(Continued)

*Primary Examiner* — Shanon A Foley
(74) *Attorney, Agent, or Firm* — Blank Rome LLP

(57) ABSTRACT

The present invention provides a novel infectious cDNA clone of porcine reproductive and respiratory syndrome virus (PRRSV), particularly for PRRSV strain VR2385; an improved DNA-launched reverse genetics system for PRRSV; infectious chimeric PRRSV viruses generated through DNA shuffling; modified live-attenuated virus vaccines (MLV) using DNA shuffled chimeric viruses; chimeric viral proteins produced through shuffled chimeric viruses; PRRSV antigens and subunit vaccines based on shuffled chimeric viral proteins; and method of producing broadly protective PRRSV vaccines using DNA shuffling techniques.

16 Claims, 9 Drawing Sheets

(56) References Cited

OTHER PUBLICATIONS

Chang, Chia-Chun J., et al.; Evolution of a Cytokine Using DNA Family Shuffling; Nature Biotechnology; (Aug. 1999); pp. 793-797; vol. 17; Nature America Inc.

Chang, C.-C., et al.; Evolution of Porcine Reproductive and Respiratory Syndrome Virus during Sequential Passages in Pigs; Journal of Virology; (May 2002); pp. 4750-4763; vol. 76; No. 10; American Society for Microbiology.

Charpentier, Charlotte, et al.; Extensive Recombination Among Human Immunodeficiency Virus Type 1 Quasispecies Makes an Important Contribution to Viral Diversity in Individual Patients; Journal of Virology; (Mar. 2006); pp. 2472-2482; vol. 80; No. 5; American Society for Microbiology.

Crameri, Andreas, et al.; DNA Shuffling of a Family of Genes from Diverse Species Accelerates Directed Evolution; Nature; (Jan. 1998); pp. 288-291; vol. 391; Nature Macmillian Publishers Ltd.

Lima, Marcelo DE, et al.; Development of a porcine Reproductive and Respiratory Syndrome Virus Differentiable (DIVA) Strain Through Deletion of Specific Immunodominant Epitopes; Vaccine; (2008); pp. 3594-3600; vol. 26; Elsevier.

Dea, S., et al.; Current Knowledge on the Structural Proteins of Porcine Reproductive and Respiratory Syndrome (PRRS) Virus: Comparison of the North American and European Isolates; Archives of Virology; (2000); pp. 659-688; vol. 145; Springer-Verlag.

Dobbe, Jessika C., et al.; Construction of Chimeric Arteriviruses Reveals that the Ectodomain of the Glycoprotein is not the Main Determinant of Equine Arteries Virus Tropism in Cell Culture; Virology; (2001); pp. 283-294; vol. 288; Academic Press.

Li, Yufeng, et al.; Genetic Analysis of Two Porcine Reproductive and Respiratory Syndrome Viruses with Different Virulence Isolated in China; Archives of Virology; (2008); pp. 1877-1884; vol. 153; Springer-Verlag.

Fang, Ying, et al.; A Full-Length cDNA Infectious Clone of North American Type 1 Porcine Reproductive and Respiratory Syndrome Virus: Expression of Green Fluorescent Protein in the Nsp2 Region; Journal of Virology; (Dec. 2006); pp. 11447-11455; vol. 80; No. 23; American Society for Microbiology.

Fang, Y., et al; Diversity and Evolution of a Newly Emerged North American Type 1 Porcine Arterivirus: Analysis of Isolates Collected Between 1999 and 2004; Archives of Virology; (2007); pp. 1009-1017; vol. 152; Springer-Verlag.

Forsberg, Roald, et al.; The Genetic Diversity of European Type PRRSV is Similar to that of the North American Type but is Geographically Skewed within Europe; Virology; (2002); pp. 38-47; vol. 299; Elsevier Science (USA).

Halbur, P., et al.; Efficacy of Antimicrobial Treatments and Vaccination Regimens for Control of Porcine Reproductive and Respiratory Syndrome Virus and *Streptococcus suis* Coinfection of Nursery Pigs; Journal of Clinical Microbiology; (Mar. 2000); pp. 1156-1160; vol. 38; No, 3; American Society for Microbiology.

Halbur, Patrick G., et al.; Development of a Streptavidin-Biotin Immunoperoxidase Procedure for the Detection of Porcine Reproductive and Respiratory Syndrome Virus Antigen in Porcine Lung; Journal of Veterinary Diagnostic Investigation; (1994); pp. 254-257; vol. 6; Sage Publications.

Halbur, P. G., et al.; Immunohistochemical Identification of Porcine Reproductive and Respiratory Syndrome Virus (PRRSV) Antigen in the Heart and Lymphoid System of Three-Week-Old Colostrum-Deprived Pigs; Veterinary Pathology Online; (1995); pp. 200-204; vol. 32; Sage Publications.

Halbur, P. G., et al.; Comparison of the Antigen Distribution of Two US porcine Reproductive and Respiratory Syndrome Virus Isolates with that of the Lelystad Virus; Veterinary Pathology Online; (1996); pp. 159-170; vol. 33; Sage Publications.

Halbur, P. G., et al; Comparison of the Pathogenicity of Two US Porcine Reproductive and Respiratory Syndrome Virus Isolates with that of the Lelystad Virus; Veterinary Pathology Online; (1995); pp. 648-660; vol. 32; Sage Publications.

Halbur, Patrick G., et al.; Comparative Pathogenicity of Nine US Porcine Reproductive and Respiratory Syndrome Virus (PRRSV) Isolates in a Five-Week-Old Cesarean-Derived, Colostrum-Derived Pig Model; Journal of Veterinary Diagnostic Investigation; (1996); pp. 11-20; vol. 8; Sage Publications.

Halbur, P. G., et al.; Effects of Different US Isolates of Porcine Reproductive and Respiratory Syndrome Virus (PRRSV) on Blood and Bone Marrow Parameters of Experimentally Infected Pigs; Veterinary Record; (2002); pp. 344-348; vol. 151; Group.bjm.com.

Hou, Yan-Hong, et al.; A Recombinant Plasmid Co-Espressing Swine Ubiquitin and the GP5 Encoding-Gene of Porcine Reproductive and Respiratory Syndrome Virus Induces Protective Immunity in Piglets; Vaccine; (2008); pp. 1438-1449; vol. 26; Elsevier.

Huang, Y. W., et al; Indentification and Characterization of a Porcine Monocytic Cell Line Supporting Porcine Reproductive and Respiratory Syndrome (PRRSV) Replication and Progeny Virion Production by using an Improved DNA-Launched PRRSV Reverse Genetics System; Virus Research; (2009); pp. 1-8; vol. 145; Elsevier.

Jiang, Wenming, et al.; Recombinant Adenovirus Expressing GP5 and M Fusion Proteins of Porcine Reporductive and Respiratory Syndrome Virus Induce Both Humoral and Cell-Mediated Immune Responses in Mice; Veterinary Immunology and Immunopathology; (2006); pp. 169-180; vol. 113; Elsevier.

Jiang, Yunbo, et al.; Immunogenicity and Protective Efficacy of Recombianat Pseudorabies Virus Expressing the Two Major Membrane-Associated Proteins of Porcine Reproductive and Respiratory Syndrome Virus; Vaccine; (2007); pp. 547-560; vol. 25; Elsevier.

Jiang, Yunbo, et al.; DNA Vaccines Co-Expressing GP5 and M Proteins of Porcine Reproductive and Respiratory Syndrome Virus (PRRSV) Display Enhanced Immunogenicity; Vaccine; (2006); pp. 2869-2879; vol. 24; Elsevier.

Key, K. F.; et al; Direct Inoculation of RNA Transcripts from an Infectious cDNA Clone of Porcine Reproductive and Respiratory Syndrome Virus (PRRSV) into the Lymph Nodes and Tonsils of Pigs Initiates PRRSV Infection in vivo; Archives of Virology; (2007); pp. 1383-1387; vol. 152; Springer-Verlag.

Key, K. F., et al.; Development of a Heteroduplex Mobility Assay to Identify Field Isolates of Porcine Reporductive and Respiratory Syndrome Virus with Nucleotide Sequences Closely Related to Those of Modified Live-Attenuated Vaccines; Journal of Clinical Microbiology; (Jun. 2003); pp. 2433-2439; vol. 41; No. 6; American Society for Microbiology.

Key, Kijona F., et al.; Genetic Variation and Phylogenetic Analyses of the ORF5 Gene of Acute Porcine Reproductive and Respiratory Syndrome Virus Isolates; Veterinary Microbiology; (2001); pp. 249-263; vol. 83; Elsevier.

Kwon, Byungjoon, et al.; Identification of Virulence Determinants of Porcine Reproductive and Respiratory Syndrome Virus Through Construction of Chimeric Clones; Virology; (2008); pp. 371-378; vol. 380; Elsevier.

Lager, K. M., et al.; Duration of Homologous Porcine Reproductive and Respiratory Syndrome Virus Immunity in Pregnant Swine; Veterinary Microbiology; (1997); pp. 127-133; vol. 58; Elsevier.

Locher, Christopher P., et al; DNA Shuffling and Screening Strategies for Improving Vaccine Efficacy; DNA and Cell Biology; (2005); pp. 256-263; vol. 24; No. 4; Mary Ann Liebert, Inc.

Lopez, O. J., et al.; Protection Against Porcine Reproductive and Respiratory Syndrome Virus (PRRSV) Infection throguh Passive Transfer of PRRSV-Neutralizinf Antibodies is Dose Dependent; Clinical and Vaccine Immunology; (Mar. 2007); pp. 269-276; vol. 14; No. 3; American Society for Microbiology.

Mardassi, Helmi, et al.; Intracellular Synthesis, Processing, and Transport of Proteins Encoded by ORFs 5 to 7 of Porcine Reproductive and Respiratory Syndrome Virus; Virology; (1996); pp. 98-112; vol. 221; Article No. 0356; Academic Press, Inc.

Martinez, E., et al.; Simultaneous Detection and Genotyping of Porcine Reproductive and Respiratory Syndrome Virus (PRRSV) by Real-Time RT-PCR and Amplicon Melting Curve Analysis using SYBR Green; Research in Veterinary Science; (2008); pp. 184-193; vol. 85; Elsevier.

Matanin, Brad M., et al.; Purification of the Major Envelop Protein GP5 of Porcine Reproductive and Respiratory Syndrome Virus (PRRSV) from Native Virions; Journal of Virological Methods; (2008); pp. 127-135; vol. 147; Elsevier.

(56) References Cited

OTHER PUBLICATIONS

Meier, William A., et al.; Cytokines and Synthetic Double-Stranded RNA Augment the T Helper 1 Immune Response of Swine to Porcine Reproductive and Respiratory Syndrome Virus; Veterinary Immunology and Immunopathology; (2004); pp. 299-314; vol. 102; Elsevier.
Meng, X. J.; Heterogeneity of Porcine Reporductive and Respiratory Syndrome Virus: Implications for Current Vaccine Efficay and Future Vaccine Development; Veterinary Microbiology; (2000); pp. 309-329; vol. 74; Elsevier.
Meng, Xiang-Jin, et al.; Molecular Cloning and Nucleotide Srquencing of the 3'-Terminal Genomic RNA of the Porcine Reproductive and Respiratory Syndrome Virus; Journal of General Virology; (1994); pp. 1795-1801; vol. 75; SGM.
Meng, Xiang-Jin, et al.; Characterization of a High-Virulence US Isolate of Porcine Reproductive and Respiratory Syndrome Virus in a Continuous Cell Line. ATCC CRL11171; Journalv of Veterinary Diagnostic Investigation; (1996); pp. 374-381; vol. 8; Sage Publications.
Meng, X. -J., et al.; Phylogenetic Analyses of the Porcine of the Putative M (ORF 6) and N (ORF 7) Genes of Porcine Reproductive and Respiratory Syndrome Virus (PRRSV): Implication for the Existence of Two Genotypes of PRRSV in the U.S.A. and Europe; Archives of Virology; (1995); pp. 745-755; vol. 140; Springer-Verlag.
Meng, Xiang-Jin, et al.; Sequence Comparison of Open Reading Frames 2 to 5 of Low and High Virulence Unites States Isolates of Porcine Reproductive and Respiratory Syndrome Virus; Journal of General Virology; (1995); pp. 3181-3188; vol. 76; SGM.
Meng, Xiang-Jin, et al.; A Nested Set of Six or Seven Subgenomic mRNAs is Formed in Cells Infected with Different Isolates of Porcine Reproductive and Respiratory Syndrome Virus; Journal or General Virology; (1996); pp. 1265-1270; vol. 77; SGM.
Meulenberg, J. J. M., et al.; Infectious Transcripts from Cloned Genome-Length cDNA of Porcine Reproductive and Respiratory Syndrome Virus; Journal of Virology; (Jan. 1998); pp. 380-387; vol. 72; No. 1; American Society for Microbiology.
Meulenberg, J. J. M., et al.; Indentification and Characterization of a Sixth Structural Protein of Lelystad Virus: The Glycoprotein GP2 Encoded by ORF2 is Incorporated in Virus Particles; Virology; (1996); pp. 44-51; vol. 225; Article No. 0573; Academic Press, Inc.
Meulenberg, Janneke J. M., et al.; Characterization of Proteins Encoded by ORFs 2 to 7 of Lelystad Virus; Virology; (1995); pp. 156-163; vol. 206; Academic Press, Inc.
Meulenberg, J. J. M., et al.; Posttranslational Processing and Identification of a Neutralization Domain of the GP4 Protein Encoded by OFR4 of Lelystad Virus; Journal of Virology; (Aug. 1997); pp. 6061-6067; vol. 71; No. 8; American Society for Microbiology.
Minshull, Jeremy, et al.; Protein Evolution by Molecular Breeding; Current Opinion in Chemical Biology; (1999); pp. 284-290; vol. 3; Elsevier Science Ltd.
Nelsen, Chris J., et al.; Porcine Reproductive and Respiratory Syndrome Virus Comparison: Divergent Evolution on Two Continents; Journal of Virology; (Jan. 1999); pp. 270-280; vol. 73; No. 1; American Society for Microbiology.
Ness, Jon E., et al.; Synthetic Shuffling Expands Functional Protein Diversity by Allowing Amino Acids to Recombine Independently; Nature Biotechnology; (Dec. 2002); pp. 1251-1255; vol. 20; Nature Publishing Group.
Ness, Jon E., et al.; DNA Shuffling of Subgenomic Sequences of Subtilsin; Nature Biotechnology; (Sep. 1999); pp. 893-896; vol. 17; Nature America Inc.
Neumann, Eric J., et al.; Assessment of the Economic Impact of Porcine Reproductive and Respiratory Syndrome on Swine Production in the United States; Vet Med Today: Food Animal Economics; (Aug. 2005); pp. 385-392; vol. 227; No. 3; JAVMA.
Nilubol, D., et al.; The Effect of a Killed Porcine Porcine Reproductive and Respiratory Syndrome Virus (PRRSV) Vaccine Treatment on Virus Shedding in Previously PRRSV Infected Pigs; Veterinary Microbiology; (2004); pp. 11-18; vol. 102; Elsevier.
Opriessnig, Tanja, et al.; Use of an Experimental Model to Test the Efficacy of planned Exposure to Live Porcine Reporductive and Respiratory Syndrome Virus; Clinical and Vaccine Immunology; (Dec. 2007); pp. 1572-1577; vol. 14; No. 12; American Society for Microbiology.

Opriessnig, T., et al.; Comparison of Molecular and Bilogical Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Fields Isolates of PRRSV; Journal of Virology; (Dec. 2002); pp. 11837-11844; vol. 76; No. 23; American Society for Microbiology.
Opriessnig, T., et al.; Effect of Porcine Cicovirus Type 2 (PCV2) Vaccination on Porcine Reproductive and Respiratory Syndrome Virus (PRRSV) and PCV2 Coinfection; Veterinary Microbiology; (2008); pp. 103-114; vol. 131; Elsevier.
Opriessnig, T., et al.; Porcine Cicovirus Type 2 Infection Decreases the Efficacy of a Modified Live Porcine Reproductive and Respiratory Syndrome Virus Vaccine; Clinical and Vaccine Immunology; (Aug. 2006); pp. 923-929; vol. 13; No. 8; American Society for Microbiology.
Osen, Wolfram, et al.; A DNA vaccine based on a Shuffled E7 Oncogene of he Human Papillmavirus Type 16 (HPV 16) Induces E7-Specific Cytotoxic T Cells but Lacks Transforming Activity; Vaccine; (2001); pp. 4276-4286; vol. 19; Elsevier.
Osorio, F. A., et al; Passive Transfer of Virus-Specific Antibodies Confers Protection Against Reproductive Failure Induced by a Virulent Strain of Porcine Reproductive and Respiratory Syndrome Virus and Establishes Sterilizing Immunity; Virology; (2002); pp. 9-20; vol. 302; Elsevier Science.
Ostrowski, M., et al.; Identification of Neutralizing and Nonneutralizing Epitopes in the Porcine Reproductive and Respiratory Syndrome Virus GP5 Ectodomain; Journal of Virology; (May 2002); pp. 4241-4250; vol. 76; No. 9; American Society for Microbiology.
Papatsiros, V. G., et al.; Long-Term Administration of a Commercial Porcine Reproductive and Respiratory Syndrome Virus (PRRSV)-Inactivated Vaccine in PRRSV-Endemically Infected Sows; J. Vet. Med.; (2006); pp. 266-272; vol. 53; Blackwell Verlag.
Patel, Deendayal, et al.; Peptide-Conjugated Morpholino Oligomers Inhibit Porcine Reproductive and Respiratory Syndrome Virus Replication; Antiviral Research; (2008); pp. 95-107; vol. 77; Elsevier.
Faaberg, Kay S., et al.; Neutralizing Antibody Responses of Pigs Infected with Natural GP5 N-Glycan Mutants of Porcine Reproductive and Respiratory Syndrome Virus; Viral Immunology; (2006); pp. 294-304; vol. 19; No. 2; Mary Ann Liebert, Inc.
Locher, Christopher P., et al.; Overcoming Antigenic Diversity and Improving Vaccines Using DNA Shuffling and Screening Technologies; Expert Opin. Biol. Ther.; (2004); pp. 589-597; No. 4; vol. 4; Ashley Publications Ltd.
Locher, Christopher P., et al.; Development of Novel Vaccines Using DNA Shuffling and Screening Strategies; Current Opinion in Molecular Therapeutics; (2004); pp. 34-39; vol. 6; No. 1; Thomson Scientific.
European Search Report dated Dec. 12, 2013.
Huang, Y.W., et al; Novel Strategies and Approaches to Develop the Next Generation of Vaccines Against Porcine Reproductive and Respiratory Syndrome Virus; (2010); pp. 141-149; vol. 154, No. 1-2, Virus Research.
Gudmundsdottir, Ingigerdur, et al; Infection of Porcine Alveolar Macrophages with Recombinant Chimeric Porcine Reproductive and Respiratory Syndrome Virus: Effects on Cellular Gene Transcription and Virus Growth; (2009); pp. 145-150; vol. 145, No. 1; Virus Research.
Ni, Yan-Yan, et al; Establishment of a DNA-launched Infectious Clone for a Highly Pneumovirulent Strain of Type 2 Porcine Reproductive and Respiratory Syndrome Virus: Identification and in vitro and in vivo Characterization of a Large Spontaneous Deletion in the nsp2 Region; (2011); vol. 160, No. 1; Virus Research.
Fang, Ying, et al.; Development of Genetic Markers in the Non-Structural Protein 2 Region of a US Type 1 Porcine Reproductive and Respiratory Syndrome Virus; Implications for Future Recombinant Marker Vaccine Development; Journal of General Virology; pp. 3086-3096; vol. 89; SGM, Dec. 2008.
G. Misinzo, et al., "Induction of Virus-Neutralizing Antibodies and Partial Virological Protection Upon Challenge," Efficacy of an Inactivated PRRSV Vaccine, pp. 449-454, (2006).

* cited by examiner

FIG. 2A    FIG. 2B
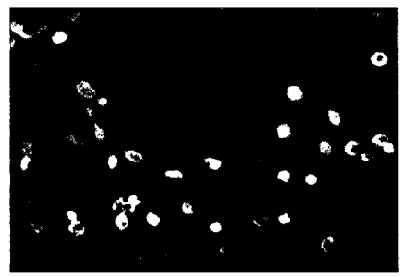
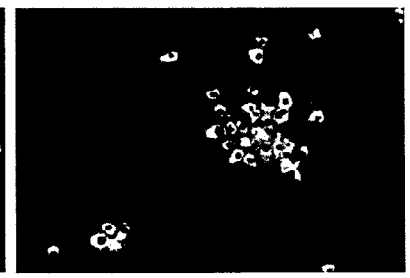
FIG. 2C    FIG. 2D
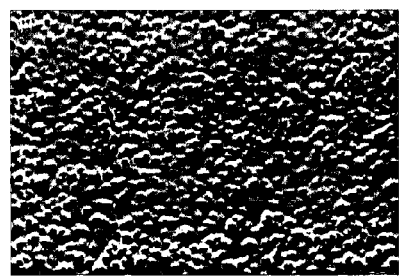
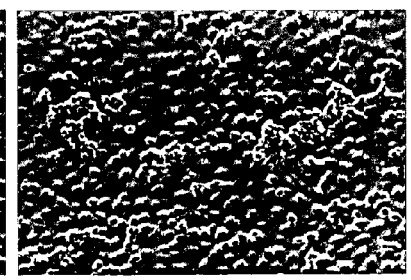
FIG. 2E    FIG. 2F

SEQUENCE LISTING

<160> NUMBER OF SEQ ID NOS: 30

<210> SEQ ID NO 1
<211> LENGTH: 22
<212> TYPE: DNA
<213> ORGANISM: Artificial Sequence
<220> FEATURE:
<223> OTHER INFORMATION: Artificially synthesized

<400> SEQUENCE: 1
atgacgtata ggtgttggct ct                                           22

<210> SEQ ID NO 2
<211> LENGTH: 19
<212> TYPE: DNA
<213> ORGANISM: Artificial Sequence
<220> FEATURE:
<223> OTHER INFORMATION: Artificially synthesized

<400> SEQUENCE: 2
gggctcaacc cttattcta                                               19

<210> SEQ ID NO 3
<211> LENGTH: 51
<212> TYPE: DNA
<213> ORGANISM: Artificial Sequence
<220> FEATURE:
<223> OTHER INFORMATION: Artificially synthesized

<400> SEQUENCE: 3
ttggatccgg cgcgcctaat acgactcact ataggatgac gtataggtgt t           51

<210> SEQ ID NO 4
<211> LENGTH: 18
<212> TYPE: DNA
<213> ORGANISM: Artificial Sequence
<220> FEATURE:
<223> OTHER INFORMATION: Artificially synthesized

<400> SEQUENCE: 4
cccaaatgga cctatcgt                                                18

<210> SEQ ID NO 5

```
<211> LENGTH: 20
<212> TYPE: DNA
<213> ORGANISM: Artificial Sequence
<220> FEATURE:
<223> OTHER INFORMATION: Artificially synthesized

<400> SEQUENCE: 5
tcagagggtt gctcaatggg                                                   20

<210> SEQ ID NO 6
<211> LENGTH: 22
<212> TYPE: DNA
<213> ORGANISM: Artificial Sequence
<220> FEATURE:
<223> OTHER INFORMATION: Artificially synthesized

<400> SEQUENCE: 6
gacctgtgtg atcggttttg cg                                                22

<210> SEQ ID NO 7
<211> LENGTH: 22
<212> TYPE: DNA
<213> ORGANISM: Artificial Sequence
<220> FEATURE:
<223> OTHER INFORMATION: Artificially synthesized

<400> SEQUENCE: 7
gtcaagggca gggtaagggc at                                                22

<210> SEQ ID NO 8
<211> LENGTH: 22
<212> TYPE: DNA
<213> ORGANISM: Artificial Sequence
<220> FEATURE:
<223> OTHER INFORMATION: Artificially synthesized

<400> SEQUENCE: 8
tggcggctag cagtttaaac ac                                                22

<210> SEQ ID NO 9
<211> LENGTH: 22
<212> TYPE: DNA
<213> ORGANISM: Artificial Sequence
<220> FEATURE:
<223> OTHER INFORMATION: Artificially synthesized

<400> SEQUENCE: 9
agcatgccct taccctgccc tt                                                22

<210> SEQ ID NO 10
<211> LENGTH: 22
<212> TYPE: DNA
<213> ORGANISM: Artificial Sequence
<220> FEATURE:
<223> OTHER INFORMATION: Artificially synthesized

<400> SEQUENCE: 10
gcctgactaa ggagcagtgt tt                                                22

<210> SEQ ID NO 11
<211> LENGTH: 20
<212> TYPE: DNA
<213> ORGANISM: Artificial Sequence
<220> FEATURE:
<223> OTHER INFORMATION: Artificially synthesized

<400> SEQUENCE: 11
```
ttggggagcg gagagctcga                                                      20

<210> SEQ ID NO 12
<211> LENGTH: 22
<212> TYPE: DNA
<213> ORGANISM: Artificial Sequence
<220> FEATURE:
<223> OTHER INFORMATION: Artificially synthesized

<400> SEQUENCE: 12
ctgatctaga agggtcgagc tc                                                   22

<210> SEQ ID NO 13
<211> LENGTH: 22
<212> TYPE: DNA
<213> ORGANISM: Artificial Sequence
<220> FEATURE:
<223> OTHER INFORMATION: Artificially synthesized

<400> SEQUENCE: 13
tggtcaacta ccaaggaacg tt                                                   22

<210> SEQ ID NO 14
<211> LENGTH: 22
<212> TYPE: DNA
<213> ORGANISM: Artificial Sequence
<220> FEATURE:
<223> OTHER INFORMATION: Artificially synthesized

<400> SEQUENCE: 14
gtcaaggaat ttacccaacg tt                                                   22

<210> SEQ ID NO 15
<211> LENGTH: 43
<212> TYPE: DNA
<213> ORGANISM: Artificial Sequence
<220> FEATURE:
<223> OTHER INFORMATION: Artificially synthesized

<400> SEQUENCE: 15
tacatatgtt tttttttttt tttttttttt tttaatttcg gcc                            43

<210> SEQ ID NO 16
<211> LENGTH: 31
<212> TYPE: DNA
<213> ORGANISM: Artificial Sequence
<220> FEATURE:
<223> OTHER INFORMATION: Artificially synthesized

<400> SEQUENCE: 16
catttcccag catggcctta ccctgccctt g                                         31

<210> SEQ ID NO 17
<211> LENGTH: 31
<212> TYPE: DNA
<213> ORGANISM: Artificial Sequence
<220> FEATURE:
<223> OTHER INFORMATION: Artificially synthesized

<400> SEQUENCE: 17
caagggcagg gtaaggccat gctgggaaat g                                         31

<210> SEQ ID NO 18
<211> LENGTH: 38
<212> TYPE: DNA

```
<213> ORGANISM: Artificial Sequence
<220> FEATURE:
<223> OTHER INFORMATION: Artificially synthesized

<400> SEQUENCE: 18
gctctagagc ataatcagcc ataccacatt tgtagagg                              38

<210> SEQ ID NO 19
<211> LENGTH: 31
<212> TYPE: DNA
<213> ORGANISM: Artificial Sequence
<220> FEATURE:
<223> OTHER INFORMATION: Artificially synthesized

<400> SEQUENCE: 19
gaaggcgcgc ctcgagatct gagtccggta g                                    31

<210> SEQ ID NO 20
<211> LENGTH: 22
<212> TYPE: DNA
<213> ORGANISM: Artificial Sequence
<220> FEATURE:
<223> OTHER INFORMATION: Artificially synthesized'

<400> SEQUENCE: 20
atgttgggga agtgcttgac cg                                              22

<210> SEQ ID NO 21
<211> LENGTH: 25
<212> TYPE: DNA
<213> ORGANISM: Artificial Sequence
<220> FEATURE:
<223> OTHER INFORMATION: Artificially synthesized

<400> SEQUENCE: 21
ctagagacga ccccatagtt ccgct                                           25

<210> SEQ ID NO 22
<211> LENGTH: 22
<212> TYPE: DNA
<213> ORGANISM: Artificial Sequence
<220> FEATURE:
<223> OTHER INFORMATION: Artificially synthesized

<400> SEQUENCE: 22
atgttgggga aatgcttgac cg                                              22

<210> SEQ ID NO 23
<211> LENGTH: 24
<212> TYPE: DNA
<213> ORGANISM: Artificial Sequence
<220> FEATURE:
<223> OTHER INFORMATION: Artificially synthesized

<400> SEQUENCE: 23
ttaaggaaga ccccattgtt ccgc                                            24

<210> SEQ ID NO 24
<211> LENGTH: 23
<212> TYPE: DNA
<213> ORGANISM: Artificial Sequence
<220> FEATURE:
<223> OTHER INFORMATION: Artificially synthesized

<400> SEQUENCE: 24
ctaaggacga ccccattgtt ccg                                             23
```

<210> SEQ ID NO 25
<211> LENGTH: 25
<212> TYPE: DNA
<213> ORGANISM: Artificial Sequence
<220> FEATURE:
<223> OTHER INFORMATION: Artificially synthesized

<400> SEQUENCE: 25
ctggcaattt gaatgttcaa gtatg                                    25

<210> SEQ ID NO 26
<211> LENGTH: 22
<212> TYPE: DNA
<213> ORGANISM: Artificial Sequence
<220> FEATURE:
<223> OTHER INFORMATION: Artificially synthesized

<400> SEQUENCE: 26
ctaaagacga ccccattgtt cc                                       22

<210> SEQ ID NO 27
<211> LENGTH: 22
<212> TYPE: DNA
<213> ORGANISM: Artificial Sequence
<220> FEATURE:
<223> OTHER INFORMATION: Artificially synthesized

<400> SEQUENCE: 27
atgttgggga aatgcttgac cg                                       22

<210> SEQ ID NO 28
<211> LENGTH: 23
<212> TYPE: DNA
<213> ORGANISM: Artificial Sequence
<220> FEATURE:
<223> OTHER INFORMATION: Artificially synthesized

<400> SEQUENCE: 28
ctaaggacga ctccattgtt ccg                                      23

<210> SEQ ID NO 29
<211> LENGTH: 24
<212> TYPE: DNA
<213> ORGANISM: Artificial Sequence
<220> FEATURE:
<223> OTHER INFORMATION: Artificially synthesized

<400> SEQUENCE: 29
gggaacagcg gctcaaattt acag                                     24

<210> SEQ ID NO 30
<211> LENGTH: 20
<212> TYPE: DNA
<213> ORGANISM: Artificial Sequence
<220> FEATURE:
<223> OTHER INFORMATION: Artificially synthesized

<400> SEQUENCE: 30
aggggtagcc gcggaaccat                                          20

MODIFIED LIVE-ATTENUATED VACCINES (MLV) CREATED BY DNA SHUFFLING AGAINST PORCINE REPRODUCTIVE AND RESPIRATORY SYNDROME VIRUS (PRRSV)

REFERENCE TO RELATED APPLICATION

The present application is a National Phase of and claims the benefit of PCT/US2011/038930, with an international filing date of Jun. 2, 2011, which in turn claims priority to U.S. Provisional Patent Application No. 61/350,685, filed Jun. 2, 2010, the entire disclosures of which are incorporated by reference herein.

STATEMENT OF GOVERNMENT SUPPORT

This invention was made with U.S. Government support under Grant Number 2008-55620-19132 awarded by the U.S. Department of Agriculture. The U.S. Government has certain rights in the invention.

FIELD OF INVENTION

The present invention relates to an infectious porcine reproductive and respiratory syndrome virus (PRRSV); a DNA-launched reverse genetics system for PRRSV; infectious chimeric PRRSV viruses generated through DNA shuffling; modified live-attenuated virus vaccines (MLV) based on the shuffled chimeric viruses; chimeric viral proteins produced through the shuffled chimeric viruses; PRRSV antigens and subunit vaccines based the shuffled chimeric viral proteins; and method of producing broadly protective PRRSV vaccines using DNA shuffling techniques against genetically diverse strains of PRRSV.

BACKGROUND OF THE INVENTION

Porcine reproductive and respiratory syndrome (PRRS) has devastated the global swine industry causing immense economic losses (Neumann, E. J., J. B. Kliebenstein, C. D. Johnson, J. W. Mabry, E. J. Bush, A. H. Seitzinger, A. L. Green, and J. J. Zimmerman. 2005. Assessment of the economic impact of porcine reproductive and respiratory syndrome on swine production in the United States. J Am Vet Med Assoc 227:385-92). Severe outbreaks continue to appear periodically worldwide. For example, a highly pathogenic pig disease ("pig high fever disease") caused by a variant strain of PRRSV recently emerged in China with 20-100% mortality. New and more severe PRRS outbreaks will likely continue to emerge worldwide. The causative agent, PRRSV, is a small, enveloped, single-stranded, positive-sense RNA virus in the family Arteriviridae (Snijder, E. J., and J. J. Meulenberg. 1998. The molecular biology of arteriviruses. J Gen Virol 79 (Pt 5):961-79). At least seven structural proteins are translated from a 3'-coterminal nested set of subgenomic mRNAs of PRRSV (Meng, X. J., P. S. Paul, I. Morozov, and P. G. Halbur. 1996. A nested set of six or seven subgenomic mRNAs is formed in cells infected with different isolates of porcine reproductive and respiratory syndrome virus. J Gen Virol 77 (Pt 6):1265-70, Snijder, E. J., and J. J. Meulenberg. 1998 (supra)). The highly polymorphic ORF5 gene encodes the major envelope protein GP5. The other major structural proteins include the M and N encoded by ORFs 6 and 7, respectively (Bautista, E. M., J. J. Meulenberg, C. S. Choi, and T. W. Molitor. 1996. Structural polypeptides of the American (VR-2332) strain of porcine reproductive and respiratory syndrome virus. Arch Virol 141:1357-65, Mardassi, H., B. Massie, and S. Dea. 1996. Intracellular synthesis, processing, and transport of proteins encoded by ORFs 5 to 7 of porcine reproductive and respiratory syndrome virus. Virology 221:98-112, Meng, X. J., P. S. Paul, and P. G. Halbur. 1994. Molecular cloning and nucleotide sequencing of the 3'-terminal genomic RNA of the porcine reproductive and respiratory syndrome virus. J Gen Virol 75 (Pt 7):1795-801, Meng, X. J., P. S. Paul, P. G. Halbur, and M. A. Lum. 1995. Phylogenetic analyses of the putative M (ORF 6) and N (ORF 7) genes of porcine reproductive and respiratory syndrome virus (PRRSV): implication for the existence of two genotypes of PRRSV in the U.S.A. and Europe. Arch Virol 140: 745-55, Meng, X. J., P. S. Paul, P. G. Halbur, and I. Morozov. 1995. Sequence comparison of open reading frames 2 to 5 of low and high virulence United States isolates of porcine reproductive and respiratory syndrome virus. J Gen Virol 76 (Pt 12):3181-8, Meulenberg, J. J., J. N. Bos-de Ruijter, R. van de Graaf, G. Wensvoort, and R. J. Moormann. 1998. Infectious transcripts from cloned genome-length cDNA of porcine reproductive and respiratory syndrome virus. J Virol 72:380-7, Meulenberg, J. J., and A. Petersen-den Besten. 1996. Identification and characterization of a sixth structural protein of Lelystad virus: the glycoprotein GP2 encoded by ORF2 is incorporated in virus particles. Virology 225:44-51, Meulenberg, J. J., A. Petersen-den Besten, E. P. De Kluyver, R. J. Moormann, W. M. Schaaper, and G. Wensvoort. 1995. Characterization of proteins encoded by ORFs 2 to 7 of Lelystad virus. Virology 206:155-63, Meulenberg, J. J., A. P. van Nieuwstadt, A. van Essen-Zandbergen, and J. P. Langeveld. 1997. Posttranslational processing and identification of a neutralization domain of the GP4 protein encoded by ORF4 of Lelystad virus. J Virol 71:6061-7). GP5 is the main protein that induces neutralizing antibodies (Ostrowski, M., J. A. Galeota, A. M. Jar, K. B. Platt, F. A. Osorio, and O. J. Lopez. 2002. Identification of neutralizing and nonneutralizing epitopes in the porcine reproductive and respiratory syndrome virus GP5 ectodomain. J Virol 76:4241-50, Plagemann, P. G. 2004. The primary GP5 neutralization epitope of North American isolates of porcine reproductive and respiratory syndrome virus. Vet Immunol Immunopathol 102:263-75), although neutralizing epitopes have also been identified in GP3, GP4 and M (Meulenberg, et al. 1997 (supra), Plana Duran, J., I. Climent, J. Sarraseca, A. Urniza, E. Cortes, C. Vela, and J. I. Casal. 1997. Baculovirus expression of proteins of porcine reproductive and respiratory syndrome virus strain Olot/91. Involvement of ORF3 and ORF5 proteins in protection. Virus Genes 14:19-29). Extensive antigenic, genetic and pathogenic variations have been documented for PRRSV (Meng, X. J. 2000. Heterogeneity of porcine reproductive and respiratory syndrome virus: implications for current vaccine efficacy and future vaccine development. Vet Microbiol 74:309-29). The nucleotide sequence identity between the European (type 1) and North American (type 2) genotypes is only about 65% (Allende, R., T. L. Lewis, Z. Lu, D. L. Rock, G. F. Kutish, A. Ali, A. R. Doster, and F. A. Osorio. 1999. North American and European porcine reproductive and respiratory syndrome viruses differ in non-structural protein coding regions. J Gen Virol 80 (Pt 2):307-15, Nelsen, C. J., M. P. Murtaugh, and K. S. Faaberg. 1999. Porcine reproductive and respiratory syndrome virus comparison: divergent evolution on two continents. J Virol 73:270-80). Even among some isolates within the type 2 North American genotype and within the type 1 European genotype, the sequences differ by more than 10% (Forsberg, R., T. Storgaard, H. S. Nielsen, M. B. Oleksiewicz, P. Cordioli, G. Sala, J. Hein, and A. Botner. 2002. The genetic diversity of European type PRRSV is similar to that of the North American type but is geographically skewed within Europe. Virology 299:38-47, Meng, Paul, Halbern and Lum, 1995 (supra), Meng, Paul, Halbur, and Morozov, 1995 (supra), Stadejek, T., M. B. Oleksiewicz, D. Potapchuk, and K. Podgorska. 2006. Porcine reproductive and respiratory syndrome virus strains of exceptional diversity in eastern Europe support the definition of new genetic subtypes. J Gen Virol 87:1835-41, Stadejek, T., M. B. Oleksiewicz, A. V. Scherbakov, A. M. Timina, J. S. Krabbe, K. Chabros, and D. Potapchuk. 2008. Definition of subtypes in the European genotype of porcine reproductive and respiratory syndrome virus: nucleocapsid characteristics and geographical distribution in Europe. Arch Virol 153:1479-88, Stadejek, T., A. Stankevicius, T. Storgaard, M. B. Oleksiewicz, S. Belak, T. W. Drew, and Z. Pejsak. 2002. Identification of radically different variants of porcine reproductive and respiratory syndrome virus in Eastern Europe: towards a common ancestor for European and American viruses. J Gen Virol 83:1861-73). There exist at least 9 major clusters of PRRSV within the type 2 North American genotype, and 4 major clusters within the type 1 European genotype (Forsberg, et al, 2002, Stadejek, et al, 2002 (supra)).

Modified-live attenuated vaccines (MLVs) against PRRSV were generally effective against homologous strains but were less effective or ineffective against heterologous strains (Ansari, I. H., B. Kwon, F. A. Osorio, and A. K. Pattnaik. 2006. Influence of N-linked glycosylation of porcine reproductive and respiratory syndrome virus GP5 on virus infectivity, antigenicity, and ability to induce neutralizing antibodies. J Virol 80:3994-4004, Bastos, R. G., O. A. Dellagostin, R. G. Barletta, A. R. Doster, E. Nelson, F. Zuckermann, and F. A. Osorio. 2004. Immune response of pigs inoculated with Mycobacterium bovis BCG expressing a truncated form of GP5 and M protein of porcine reproductive and respiratory syndrome virus. Vaccine 22:467-74, de Lima, M., B. Kwon, I. H. Ansari, A. K. Pattnaik, E. F. Flores, and F. A. Osorio. 2008. Development of a porcine reproductive and respiratory syndrome virus differentiable (DIVA) strain through deletion of specific immunodominant epitopes. Vaccine 26:3594-600, Kwon, B., I. H. Ansari, A. K. Pattnaik, and F. A. Osorio. 2008. Identification of virulence determinants of porcine reproductive and respiratory syndrome virus through construction of chimeric clones. Virology 380:371-8, Lopez, 0. J., M. F. Oliveira, E. A. Garcia, B. J. Kwon, A. Doster, and F. A. Osorio. 2007. Protection against porcine reproductive and respiratory syndrome virus (PRRSV) infection through passive transfer of PRRSV-neutralizing antibodies is dose dependent. Clin Vaccine Immunol 14:269-75, Misinzo, G., P. L. Delputte, P. Meerts, C. Drexler, and H. J. Nauwynck. 2006. Efficacy of an inactivated PRRSV vaccine: induction of virus-neutralizing antibodies and partial virological protection upon challenge. Adv Exp Med Biol 581:449-54, Nilubol, D., K. B. Platt, P. G. Halbur, M. Torremorell, and D. L. Harris. 2004. The effect of a killed porcine reproductive and respiratory syndrome virus (PRRSV) vaccine treatment on virus shedding in previously PRRSV infected pigs. Vet Microbiol 102:11-8, Osorio, F. A., J. A. Galeota, E. Nelson, B. Brodersen, A. Doster, R. Wills, F. Zuckermann, and W. W. Laegreid. 2002. Passive transfer of virus-specific antibodies confers protection against reproductive failure induced by a virulent strain of porcine reproductive and respiratory syndrome virus and establishes sterilizing immunity. Virology 302:9-20, Papatsiros, V. G., C. Alexopoulos, S. K. Kritas, G. Koptopoulos, H. J. Nauwynck, M. B. Pensaert, and S. C. Kyriakis. 2006. Long-term administration of a commercial porcine reproductive and respiratory syndrome virus (PRRSV)-inactivated vaccine in PRRSV-endemically infected sows. J Vet Med B Infect Dis Vet Public Health 53:266-72, Zuckermann, F. A., E. A. Garcia, I. D. Luque, J. Christopher-Hennings, A. Doster, M. Brito, and F. Osorio. 2007. Assessment of the efficacy of commercial porcine reproductive and respiratory syndrome virus (PRRSV) vaccines based on measurement of serologic response, frequency of gamma-IFN-producing cells and virological parameters of protection upon challenge. Vet Microbiol 123:69-85). Commercial killed vaccines, except for farm-specific autogenous products, are not available in the U.S. The outcomes of the use of killed vaccines in other countries are not promising (Lager, K. M., W. L. Mengeling, and S. L. Brockmeier. 1997. Duration of homologous porcine reproductive and respiratory syndrome virus immunity in pregnant swine. Vet Microbiol 58:127-33, Misinzo, et al, 2006 (supra)).

It is thus important to develop broadly-protective and more effective PRRSV vaccines that would confer protection against a broad range of genetically diverse field isolates of PRRSV.

SUMMARY OF THE INVENTION

The present invention provides a nucleic acid molecule of a porcine reproductive and respiratory syndrome virus (PRRSV) comprising a deoxyribonucleic acid molecule encoding a complimentary sequence of PRRSV genome. In one embodiment of the invention, the PRRSV genome sequence is derived from PRRSV strain VR2385.

The present invention also provides a biologically functional plasmid or viral vector comprising a deoxyribonucleic acid molecule encoding a complimentary sequence of PRRSV genome.

The present invention further provides a biologically functional plasmid or viral vector comprising a deoxyribonucleic acid molecule encoding a complimentary sequence of PRRSV genome, wherein the complimentary sequence of PRRSV genome is flanked by a first ribozyme at the 5' end and a second ribozyme at the 3' end. In one embodiment of the invention, the first and second ribozymes comprise at least one of hammerhead ribozyme (HHRz) or hepatitis delta virus ribozyme (HDVRz). In another embodiment of the invention, the transcription of the complimentary sequence of PRRSV genome is under the control of a eukaryotic promoter. In a further embodiment of the invention, the eukaryotic promoter is a cytomegalovirus (CMV) promoter. In yet another embodiment of the invention, the eukaryotic promoter is a hybrid promoter composed of the CMV immediate early enhancer fused to a chicken beta-actin-promoter.

Additionally, the present invention provides a suitable host cell transfected by a biologically functional plasmid or viral vector comprising a deoxyribonucleic acid molecule encoding a complimentary sequence of PRRSV genome.

Further, the present invention provides a method for producing infectious PRRSV comprising transfecting a suitable host cell with a biologically functional plasmid or viral vector comprising a deoxyribonucleic acid molecule encoding a complimentary sequence of PRRSV genome.

The present invention also provides an infectious chimeric PRRSV comprising at least one viral protein that is chimeric of a plurality of genetically distinct strains. In one aspect of the invention, the at least one chimeric viral protein is at least one of viral proteins GP2, GP3, GP4, GP5, M as well as non-structural proteins (nsps). In a particular embodiment of the invention, the at least one chimeric viral protein is GP5. In a further embodiment of the invention, the GP5 viral protein is chimeric from at least two of genetically distinct strains, such as VR2385, FL12, MN184, DQ474837 (C), and JXA1.

In another aspect of the invention, the at least one chimeric viral protein is produced via DNA shuffling.

The present invention further provides an avirulent infectious chimeric PRRSV derived from chimeric infectious PRRSV.

Additionally, the present invention provides an inactivated chimeric PRRSV derived from infectious chimeric PRRSV.

The present invention further provides a chimeric PRRSV viral protein that is chimeric of a plurality of multiple genetically diverse strains. In one aspect of the invention, the chimeric viral protein is at least one of viral proteins GP2, GP3, GP4, GP5, M, and non-structural proteins (nsps). In one embodiment of the invention, the chimeric viral protein is GP5. In a further embodiment of the invention, the GP5 viral protein is chimeric from at least two of genetically distinct strains, such as strains VR2385, FL12, MN184, DQ474837 (C), and JXA1. In another aspect of the invention, the chimeric viral protein is produced via DNA shuffling.

The present invention also provides a modified live PRRSV vaccine derived from infectious chimeric PRRSV, preferably generated by DNA shuffling of GP5, as well as other PRRSV genes; a killed PRRSV vaccine derived from infectious chimeric PRRSV; and a subunit PRRSV vaccine comprising shuffled chimeric PRRSV viral protein. The vaccines protect against PRRSV infection. In one aspect of the invention, the vaccine further contains an adjuvant.

The present invention further provides a method of immunizing a pig against PRRSV viral infection, comprising administering to a pig an immunologically effective amount of a modified live PRRSV vaccine derived from chimeric PRRSV; a killed PRRSV vaccine derived from chimeric PRRSV; or a subunit PRRSV vaccine comprising chimeric PRRSV viral protein. According to one aspect of the invention, the method comprises administering the vaccine parenterally, intranasally, intradermally, or transdermally to the pig. According to another aspect of the invention, the method comprises administering the vaccine intralymphoidly or intramuscularly to the pig.

Additionally, the present invention provides a method of protecting a pig against porcine reproductive and respiratory syndrome, comprising administering to a pig an immunologically effective amount of a modified live PRRSV vaccine derived from chimeric PRRSV; a killed PRRSV vaccine derived from chimeric PRRSV; or a subunit PRRSV vaccine comprising chimeric PRRSV viral protein.

Further, the present invention provides a method for producing infectious chimeric PRRSV viruses, comprising mixing deoxyribonucleic acid molecules derived from a plurality strain of PRRSV encoding at least one viral protein, limited digestion of the deoxyribonucleic acid molecules by using a nonspecific deoxy nuclease, extending the digested deoxyribonucleic acid molecules via polymerase chain reaction without adding primer, amplifying chimeric, deoxyribonucleic acid molecules encoding the at least one PRRSV viral protein, inserting the amplified chimeric deoxyribonucleic acid molecules into an infectious deoxyribonucleic acid clone of PRRSV, and infecting a host cell with the infectious deoxyribonucleic acid clone of PRRSV. In one aspect of the invention, the infectious deoxyribonucleic acid clone of PRRSV comprising a first ribozyme at the 5' end of a complimentary sequence of PRRSV genome and a second ribozyme at the 3' end of the complimentary sequence of PRRSV genome. In a further aspect of the invention, the complimentary sequence of PRRSV genome is under the control of a eukaryotic promoter.

BRIEF DESCRIPTION OF THE DRAWINGS

The above-mentioned features of the invention will become more clearly understood from the following detailed description of the invention read together with the drawings in which:

FIGS. 2(A)-(F) illustrate an example of rescue and passage of infectious VR2385 clone. FIGS. 2(A) and (B) show IFA results from BHK-21 cells at 24 hr and 48 hr post-transfection with RNA from the full-length clone. In FIGS. 2(C) and (D), MARC-145 cells were infected with cloned virus rescued from FIGS. 2(A) and (B). FIG. 2(E) shows mock-infected cells. FIG. 2(F) illustrates cytopathic effect of MARC-145 infected with cloned PRRSV rescued from BHK.

FIG. 3(a) is a diagram of 3 PRRSV full-length cDNA clones used in the RNA-based rescue system (pSD01-08-GFP) and DNA-launched system without (pTri-PGXG) or with ribozyme elements (pTri-53Rz-PGXG). All 3 plasmids harbor the same sequence of PRRSV with EGFP gene inserted in nsp2. pT7 (open pentagon), pCAG (notched arrow with stripes), and IE (open rectangle) upstream PRRSV genome represented T7 RNA polymerase promoter, chicken β-actin promoter and intron element, respectively. The downstream elements internal ribosome entry site (IRES), neomycin resistance gene (Neo) and rabbit β-globin terminator (RBG) were indicated by a black thin arrow, a solid rectangle, and a "stop" symbol, respectively. Hammerhead ribozyme (HHRz) and hepatitis delta virus ribozyme (HDVRz) engineered at the 5'- and 3'-terminus in clone pTri-53Rz-PGXG were also indicted. FIG. 3(b) illustrates a comparison of the rescue efficiency (GFP expression level) BHK-21 (upper 3 panels) or MARC-145 cells (lower 3 panels) transfected with capped RNA transcripts from clone pSD01-08-GFP, plasmid DNA of pTri-PGXG, and plasmid DNA of pTri-53Rz-PGXG, respectively.

DETAILED DESCRIPTION OF THE INVENTION

Figure 1:
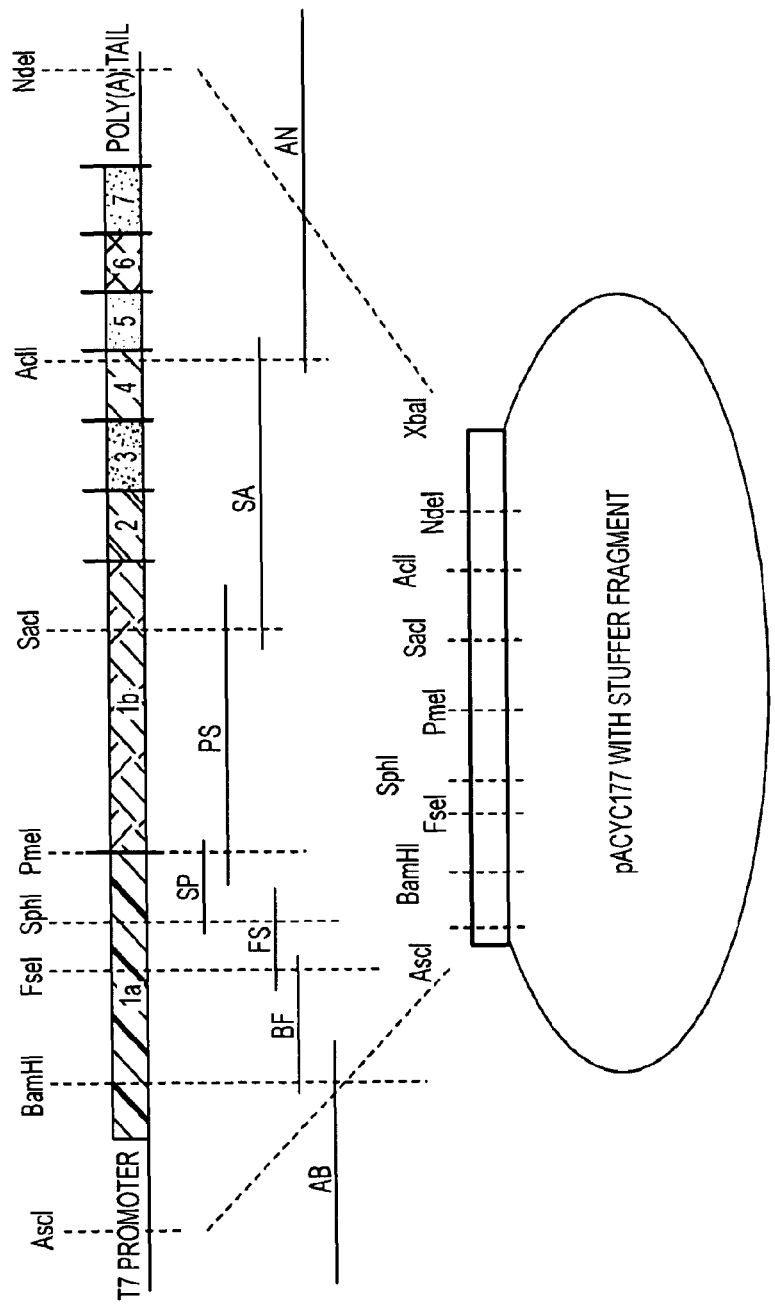
FIG. 1 is a schematic representation of the construction of VR2385 infectious cDNA clone. Each fragment was ligated stepwise into the pACYC177 vector with a stuffer fragment, resulting in the assembly of a full-length cDNA clone.

Porcine reproductive and respiratory syndrome virus (PRRSV) is arguably the most economically important swine pathogen worldwide. The current available vaccines were generally effective against homologous strains, but were less effective or ineffective against heterologous strains. Given the degree of genetic diversity observed among PRRSV strains, it is not surprising to see that the current vaccines, which are all based on a single strain, do not confer effective protection against heterologous field strains. The observed genetic diversity among field isolates will continue to be the major obstacle for PRRS control.

The fact that these current vaccines do provide protection against homologous strains indicates that vaccination with a broadly protective vaccine is still a viable control strategy against PRRS. Given the degree of genetic diversity observed among PRRSV strains, it is unlikely that a vaccine based on a single strain will confer effective broad protection against heterologous field strains. The effectiveness of a vaccine against heterologous strains will largely depend on the genetic relatedness of the virus strain to which the vaccinated animals were exposed. The present invention thus takes into consideration the genetic diversity of PRRSV for providing vaccines with broad protection against different PRRSV field isolates.

Molecular breeding through DNA shuffling-directed evolution mimics and accelerates nature's recombination strategy to direct the evolution of viruses or viral proteins in vitro (Chang, C. C., T. T. Chen, B. W. Cox, G. N. Dawes, W. P. Stemmer, J. Punnonen, and P. A. Patten. 1999. Evolution of a cytokine using DNA family shuffling. Nat Biotechnol 17:793-7, Crameri, A., S. A. Raillard, E. Bermudez, and W. P. Stemmer. 1998. DNA shuffling of a family of genes from diverse species accelerates directed evolution. Nature 391:288-91, Ness, J. E., S. Kim, A. Gottman, R. Pak, A. Krebber, T. V. Borchert, S. Govindarajan, E. C. Mundorff, and J. Minshull. 2002. Synthetic shuffling expands functional protein diversity by allowing amino acids to recombine independently. Nat Biotechnol 20:1251-5, Ness, J. E., M. Welch, L. Giver, M. Bueno, J. R. Cherry, T. V. Borchert, W. P. Stemmer, and J. Minshull. 1999. DNA shuffling of subgenomic sequences of subtilisin. Nat Biotechnol 17:893-6, Stemmer, W. P. 1994. Rapid evolution of a protein in vitro by DNA shuffling. Nature 370:389-91). For many years, modern human have repeatedly bred crops and livestock through sexual breeding to select new strains with desired traits (Locher, C. P., M. Paidhungat, R. G. Whalen, and J. Punnonen. 2005. DNA shuffling and screening strategies for improving vaccine efficacy. DNA Cell Biol 24:256-63). However, unlike sexual breeding which is limited to two parents, molecular breeding can include multiple parental strains (or genes) at a vastly accelerated rate. DNA shuffling does not require an understanding of the number or location of neutralizing epitopes on a given viral protein; it simply relies on a functional screen for the desired improvements of the shuffled viruses or proteins (Apt, D., K. Raviprakash, A. Brinkman, A. Semyonov, S. Yang, C. Skinner, L. Diehl, R. Lyons, K. Porter, and J. Punnonen. 2006. Tetravalent neutralizing antibody response against four dengue serotypes by a single chimeric dengue envelope antigen. Vaccine 24:335-44, Soong, N. W., L. Nomura, K. Pekrun, M. Reed, L. Sheppard, G. Dawes, and W. P. Stemmer. 2000. Molecular breeding of viruses. Nat Genet 25:436-9). In the DNA shuffling method for breeding viruses, a set of related parental viral genomes is first selected, subsequently digested with DNase I to create a pool of short DNA fragments. This pool of short DNA fragments is then reassembled by repeated thermocycling and amplification in the presence of DNA polymerase (Locher, C. P., V. Heinrichs, D. Apt, and R. G. Whalen. 2004. Overcoming antigenic diversity and improving vaccines using DNA shuffling and screening technologies. Expert Opin Biol Ther 4:589-97, Locher, C. P., N. W. Soong, R. G. Whalen, and J. Punnonen. 2004. Development of novel vaccines using DNA shuffling and screening strategies. Curr Opin Mol Ther 6:34-9, Minshull, J., and W. P. Stemmer. 1999. Protein evolution by molecular breeding. Curr Opin Chem Biol 3:284-90, Zhao, H., L. Giver, Z. Shao, J. A. Affholter, and F. H. Arnold. 1998. Molecular evolution by staggered extension process (StEP) in vitro recombination. Nat Biotechnol 16:258-61). The shuffled (or reassembled) chimeric viruses will then be screened and selected for desired properties such as broadly protective vaccine candidates for heterologous protection (Abrahamson, D. R., A. Powers, and R. Rodewald. 1979. Intestinal absorption of immune complexes by neonatal rats: a route of antigen transfer from mother to young. Science 206:567-9, Apt, et al, 2006 (supra), Burgers, W. A., J. H. van Harmelen, E. Shephard, C. Adams, T. Mgwebi, W. Bourn, T. Hanke, A. L. Williamson, and C. Williamson. 2006. Design and preclinical evaluation of a multigene human immunodeficiency virus type 1 subtype C DNA vaccine for clinical trial. J Gen Virol 87:399-410, Osen, W., T. Peiler, P. Ohlschlager, S. Caldeira, S. Faath, N. Michel, M. Muller, M. Tommasino, I. Jochmus, and L. Gissmann. 2001. A DNA vaccine based on a shuffled E7 oncogene of the human papillomavirus type 16 (HPV 16) induces E7-specific cytotoxic T cells but lacks transforming activity. Vaccine 19:4276-86, Raviprakash, K., D. Apt, A. Brinkman, C. Skinner, S. Yang, G. Dawes, D. Ewing, S. J. Wu, S. Bass, J. Punnonen, and K. Porter. 2006. A chimeric tetravalent dengue DNA vaccine elicits neutralizing antibody to all four virus serotypes in rhesus macaques. Virology 353:166-73), novel cell tropism of the viruses (Soong, et al, 2000 (supra), Toth, R. L., G. P. Pogue, and S. Chapman. 2002. Improvement of the movement and host range properties of a plant virus vector through DNA shuffling. Plant J 30:593-600, Tsuji, T., M. Onimaru, and H. Yanagawa. 2006. Towards the creation of novel proteins by block shuffling. Comb Chem High Throughput Screen 9:259-69), and improved virus fitness and gene function (Charpentier, C., T. Nora, O. Tenaillon, F. Clavel, and A. J. Hance. 2006. Extensive recombination among human immunodeficiency virus type 1 quasispecies makes an important contribution to viral diversity in individual patients. J Virol 80:2472-82, Pekrun, K., R. Shibata, T. Igarashi, M. Reed, L. Sheppard, P. A. Patten, W. P. Stemmer, M. A. Martin, and N. W. Soong. 2002. Evolution of a human immunodeficiency virus type 1 variant with enhanced replication in pig-tailed macaque cells by DNA shuffling. J Virol 76:2924-35, Powell, S. K., M. A. Kaloss, A. Pinkstaff, R. McKee, I. Burimski, M. Pensiero, E. Otto, W. P. Stemmer, and N. W. Soong. 2000. Breeding of retroviruses by DNA shuffling for improved stability and processing yields. Nat Biotechnol 18:1279-82). Molecular breeding through DNA shuffling can improve vaccine efficacy by increasing vaccine immunogenicity, and broadening vaccine cross-protective range for a number of viruses (Apt, et al, 2006 (supra), Brideau-Andersen, A. D., X. Huang, S. C. Sun, T. T. Chen, D. Stark, I. J. Sas, L. Zadik, G. N. Dawes, D. R. Guptill, R. McCord, S. Govindarajan, A. Roy, S. Yang, J. Gao, Y. H. Chen, N. J. Skartved, A. K. Pedersen, D. Lin, C. P. Locher, I. Rebbapragada, A. D. Jensen, S. H. Bass, T. L. Nissen, S. Viswanathan, G. R. Foster, J. A. Symons, and P. A. Patten. 2007. Directed evolution of gene-shuffled IFN-alpha molecules with activity profiles tailored for treatment of chronic viral diseases. Proc Natl Acad Sci USA 104:8269-74, Locher, et al, 2004, Expert Opin Biol Ther (supra), Locher, et al, 2005 (supra), Locher, et al, 2004, Curr Opin Mol Ther (supra), Raviprakash, et al, 2006 (supra), Whalen, R. G., R. Kaiwar, N. W. Soong, and J. Punnonen. 2001. DNA shuffling and vaccines. Curr Opin Mol Ther 3:31-6, Zhang, X. X., Q. Deng, S. Y. Zhang, J. Liu, Q. Cai, Z. M. Lu, and Y. Wang. 2003. Broadly cross-reactive mimotope of hypervariable region 1 of hepatitis C virus derived from DNA shuffling and screened by phage display library. J Med Virol 71:511-7).

It is one of the objectives of this invention to develop a chimeric, broadly-protective, modified live-attenuated vaccine (MLV) against PRRSV by molecular breeding of PRRSV via DNA shuffling, preferably through DNA shuffling of PRRSV genes, for example, with limitation, GP2, GP3, GP4, GP5, M, or non structural proteins (nsp). It is another objective of this invention to develop a chimeric subunit protein vaccine using the shuffled chimeric PRRSV proteins.

Particularly, the present invention relates to the development of novel modified live-attenuated vaccines (MLV) and subunit protein vaccine against PRRSV by using the state-of-the-art molecular breeding and DNA shuffling technology. In this invention, the inventors successfully constructed an infectious cDNA clone of a type 2 North American strain (strain ATCC VR2385) of PRRSV, and also successfully developed an improved DNA-launched reverse genetics system for PRRSV VR2385. The inventors successfully conducted DNA shuffling experiments and demonstrated that the major envelope protein gene GP5 from 5 genetically distinct strains of PRRSV can be successfully bred through DNA-shuffling, and infectious chimeric viruses were successfully rescued. The shuffled chimeric viruses represent all 5 genetically distinct parental strains of PRRSV as confirmed by sequence analyses of the rescued chimeric viruses. The rescued chimeric viruses are well suited for a MLV candidate. One skilled in the art, by applying conventional techniques, can readily convert the rescued chimeric viruses to a MLV. Similar DNA-shuffling approaches can be applied to other structural and non-structural genes of PRRSV, for example without limitation, GP2, GP3, GP4, M, and other nsps to develop additional modified live-attenuated chimeric virus vaccines that confer broad protection against genetically divergent strains of PRRSV. In addition, the shuffled chimeric GP5 protein along with shuffled chimeric M, GP2, GP3, GP4, or nsp proteins can serve as improved broadly-protective subunit protein vaccines against PRRSV infection.

Vaccines of the infectious viral and molecular DNA clones, and methods of using them, are also included within the scope of the present invention. Inoculated pigs are protected from serious viral infection and other diseases caused by PRRSV infection or co-infection. The novel method protects pigs in need of protection against viral infection by administering to the pig an immunologically effective amount of a vaccine according to the invention, such as, for example, a vaccine comprising an immunogenic amount of chimeric heterogeneous PRRSV viruses, particularly chimeric heterogeneous viruses comprising heterogeneous viral structural and non-structural proteins, for example without limitation, PRRSV viral proteins M, GP2, GP3, GP4, GP5, or nsp. The heterogeneous attenuated PRRSV viruses preferably comprise chimeric viruses in at least one viral structural protein gene of a plurality of multiple genetically distinct isolates. A preferred method of producing heterogeneous chimeric attenuated PRRSV viruses is through molecular breeding via DNA-shuffling technology. The preferred live chimeric virus of the present invention provides vaccines that represent genetically distinct PRRSV isolates, and provide broad protection against infection from diverse field isolates.

The vaccines comprise, for example, the infectious chimeric viral and molecular DNA clones, chimeric PRRSV infectious DNA genome in suitable plasmids or vectors, an avirulent, live shuffled chimeric virus, an inactivated shuffled chimeric virus, etc., in combination with a nontoxic, physiologically acceptable carrier and, optionally, one or more adjuvants. The vaccine may also comprise the infectious attenuated PRRSV chimeric viruses described herein. The modified live virus being most preferred.

Vaccines and methods of using them are also included within the scope of the present invention. Inoculated pigs are protected from serious viral infection of PRRSV, such as PRRS, and other related illness. The vaccines comprise, for example, heterogeneous chimeric PRRSV viruses, a nontoxic, physiologically acceptable carrier and, optionally, one or more adjuvants.

The adjuvant, which may be administered in conjunction with the vaccine of the present invention, is a substance that increases the immunological response of the pig to the vaccine. The adjuvant may be administered at the same time and at the same site as the vaccine, or at a different time, for example, as a booster. Adjuvants also may advantageously be administered to the pig in a manner or at a site different from the manner or site in which the vaccine is administered. Suitable adjuvants include, but are not limited to, aluminum hydroxide (alum), immunostimulating complexes (IS-COMS), non-ionic block polymers or copolymers, cytokines (like IL-1, IL-2, IL-7, IFN-α, IFN-γ, etc.), saponins, monophosphoryl lipid A (MLA), muramyl dipeptides (MDP) and the like. Other suitable adjuvants include, for example, aluminum potassium sulfate, heat-labile or heat-stable enterotoxin isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde.

The vaccines may further contain additional antigens to promote the immunological activity of the heterogeneous chimeric PRRSV viruses, such as other infectious swine agents and immune stimulants.

The new vaccines of this invention are not restricted to any particular type or method of preparation. The heterogeneous chimeric viral vaccines include, but are not limited to, infectious DNA vaccines (i.e., using plasmids, vectors or other conventional carriers to directly inject DNA into pigs), live vaccines, modified live vaccines, inactivated vaccines, subunit vaccines, attenuated vaccines, genetically engineered vaccines, etc. These vaccines are prepared by standard methods known in the art.

Additional genetically engineered vaccines, which are desirable in the present invention, are produced by techniques known in the art. Such techniques involve, but are not limited to, further manipulation of recombinant DNA, modification of or substitutions to the amino acid sequences of the recombinant proteins and the like.

Genetically engineered vaccines based on recombinant DNA technology are made, for instance, by identifying alternative portions of the viral gene encoding proteins responsible for inducing a stronger immune or protective response in pigs (e.g., proteins derived from M, GP2, GP3, GP4, or GP5, etc.). Various subtypes or isolates of the viral protein genes can be subjected to the DNA-shuffling method. The resulting heterogeneous chimeric viral proteins can be used broad protecting subunit vaccines. Alternatively, such chimeric viral genes or immuno-dominant fragments can be cloned into standard protein expression vectors, such as the baculovirus vector, and used to infect appropriate host cells (see, for example, O'Reilly et al., "Baculovirus Expression Vectors: A Lab Manual," Freeman & Co., 1992). The host cells are cultured, thus expressing the desired vaccine proteins, which can be purified to the desired extent and formulated into a suitable vaccine product.

If the clones retain any undesirable natural abilities of causing disease, it is also possible to pinpoint the nucleotide sequences in the viral genome responsible for any residual virulence, and genetically engineer the virus avirulent through, for example, site-directed mutagenesis. Site-directed mutagenesis is able to add, delete or change one or more nucleotides (see, for instance, Zoller et al., DNA 3:479-488, 1984). An oligonucleotide is synthesized containing the desired mutation and annealed to a portion of single stranded viral DNA. The hybrid molecule, which results from that procedure, is employed to transform bacteria. Then double-stranded DNA, which is isolated containing the appropriate mutation, is used to produce full-length DNA by ligation to a restriction fragment of the latter that is subsequently transfected into a suitable cell culture. Ligation of the genome into the suitable vector for transfer may be accomplished through any standard technique known to those of ordinary skill in the art. Transfection of the vector into host cells for the production of viral progeny may be done using any of the conventional methods such as calcium-phosphate or DEAE-dextran mediated transfection, electroporation, protoplast fusion and other well-known techniques (e.g., Sambrook et al., "Molecular Cloning: A Laboratory Manual," Cold Spring Harbor Laboratory Press, 1989). The cloned virus then exhibits the desired mutation. Alternatively, two oligonucleotides can be synthesized which contain the appropriate mutation. These may be annealed to form double-stranded DNA that can be inserted in the viral DNA to produce full-length DNA.

An immunologically effective amount of the chimeric virus or protein vaccines of the present invention is administered to a pig in need of protection against viral infection. The immunologically effective amount or the immunogenic amount that inoculates the pig can be easily determined or readily titrated by routine testing. An effective amount is one in which a sufficient immunological response to the vaccine is attained to protect the pig exposed to the PRRSV virus. Preferably, the pig is protected to an extent in which one to all of the adverse physiological symptoms or effects of the viral disease are significantly reduced, ameliorated or totally prevented.

The vaccine can be administered in a single dose or in repeated doses. Dosages may range, for example, from about 1 microgram to about 1,000 micrograms of the plasmid DNA containing the infectious chimeric DNA genome (dependent upon the concentration of the immuno-active component of the vaccine), preferably 100 to 200 micrograms of the chimeric PRRSV1-2 DNA clone, but should not contain an amount of virus-based antigen sufficient to result in an adverse reaction or physiological symptoms of viral infection. Methods are known in the art for determining or titrating suitable dosages of active antigenic agent to find minimal effective dosages based on the weight of the pig, concentration of the antigen and other typical factors. Preferably, the infectious viral DNA clone is used as a vaccine, or a live infectious virus can be generated in vitro and then the live virus is used as a vaccine. In that case, from about 50 to about 10,000 of the 50% tissue culture infective dose ($TCID_{50}$) of live virus, for example, can be given to a pig.

The novel vaccines of this invention are not restricted to any particular type or method of preparation. The vaccines include, but are not limited to, modified live vaccines, inactivated vaccines, subunit vaccines, attenuated vaccines, genetically engineered vaccines, etc.

The advantages of live shuffled chimeric vaccines are that all possible immune responses are activated in the recipient of the vaccine, including systemic, local, humoral and cell-mediated immune responses. The disadvantages of live shuffled chimeric virus vaccines, which may outweigh the advantages, lie in the potential for contamination with live adventitious viral agents or the risk that the virus may revert to virulence in the field.

To prepare inactivated virus vaccines, for instance, the virus propagation and virus production can occur in cultured porcine cell lines, such as, without limitation, MARC-145 and ATCC CRL11171 cells. Serial virus inactivation is then optimized by protocols generally known to those of ordinary skill in the art or, preferably, by the methods described herein.

Inactivated virus vaccines may be prepared by treating the chimeric PRRSV viruses with inactivating agents such as formalin or hydrophobic solvents, acids, etc., by irradiation with ultraviolet light or X-rays, by heating, etc. inactivation is conducted in a manner understood in the art. For example, in chemical inactivation, a suitable virus sample or serum sample containing the virus is treated for a sufficient length of time with a sufficient amount or concentration of inactivating agent at a sufficiently high (or low, depending on the inactivating agent) temperature or pH to inactivate the virus inactivation by heating is conducted at a temperature and for a length of time sufficient to inactivate the virus. Inactivation by irradiation is conducted using a wavelength of light or other energy source for a length of time sufficient to inactivate the virus. The virus is considered inactivated if it is unable to infect a cell susceptible to infection.

Genetically engineered vaccines, are produced by techniques known in the art. Such techniques involve, but are not limited to, the use of RNA, recombinant DNA, recombinant proteins, live viruses and the like.

For instance, after purification, the wild-type virus may be isolated from suitable clinical, biological samples such as serum, fecal, saliva, semen and tissue samples by methods known in the art, preferably by the method taught herein using infected pigs or infected suitable cell lines. The RNA is extracted from the biologically pure virus or infectious agent by methods known in the art, and purified by methods known in the art, preferably by ultracentrifugation in a CsCl gradient or other purification methods. Complementary DNA (cDNA) sequence of the viral RNA genome can be synthesized via conventional reverse transcription methods. The cDNA of viral genome is cloned into a suitable host by methods known in the art (see Maniatis et al id.), and the virus genome is then analyzed to determine essential regions of the genome for producing antigenic portions of the virus. Thereafter, the procedure is generally the same as that for the modified live vaccine, an inactivated vaccine or a subunit vaccine.

Alternatively, DNA from the isolated chimeric PRRSV, which encode one or more viral proteins can be inserted into live vectors, such as a poxvirus or an adenovirus and used as a vaccine.

An immunologically effective amount of the vaccine of the present invention is administered to a porcine or mammalian species in need of protection against said infection or syndrome. The "immunologically effective amount" can be easily determined or readily titrated by routine testing. An effective amount is one in which a sufficient immunological response to the vaccine is attained to protect the pig or other mammal exposed to the PRRSV virus which may cause PRRS, or related illness, such as "pig high fever disease." Preferably, the pig or other mammalian species is protected to an extent in which one to all of the adverse physiological symptoms or effects of the viral disease are found to be significantly reduced, ameliorated or totally prevented.

The vaccine can be administered in a single dose or in repeated doses. Dosages may contain, for example, from 1 to 1,000 micrograms of virus-based antigen (dependent upon the concentration of the immuno-active component of the vaccine), but should not contain an amount of virus-based antigen sufficient to result in an adverse reaction or physiological symptoms of viral infection. Methods are known in the art for determining or titrating suitable, dosages of active antigenic agent based on the weight of the bird or mammal, concentration of the antigen and other typical factors.

The vaccine can be administered to pigs. Also, the vaccine can be given to humans such as pig farmers who are at high risk of being infected by the viral agent. The vaccine can conveniently be administered orally, intrabuccally, intranasally, transdermally, parenterally, etc. The parenteral route of administration includes, but is not limited to, intramuscular, intravenous, intraperitoneal and subcutaneous routes.

When administered as a liquid, the present vaccine may be prepared in the form of an aqueous solution, a syrup, an elixir, a tincture and the like. Such formulations are known in the art and are typically prepared by dissolution of the antigen and other typical additives in the appropriate carrier or solvent systems. Suitable carriers or solvents include, but are not limited to, water, saline, ethanol, ethylene glycol, glycerol, etc. Typical additives are, for example, certified dyes, flavors, sweeteners and antimicrobial preservatives such as thimerosal (sodium ethylmercurithiosalicylate). Such solutions may be stabilized, for example, by addition of partially hydrolyzed gelatin, sorbitol or cell culture medium, and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Liquid formulations also may include suspensions and emulsions which contain suspending or emulsifying agents in combination with other standard co-formulants. These types of liquid formulations may be prepared by conventional methods. Suspensions, for example, may be prepared using a colloid mill. Emulsions, for example, may be prepared using a homogenizer.

Parenteral formulations, designed for injection into body fluid systems, require proper isotonicity and pH buffering to the corresponding levels of mammalian body fluids. Isotonicity can be appropriately adjusted with sodium chloride and other salts as needed. Suitable solvents, such as ethanol or propylene glycol, can be used to increase the solubility of the ingredients in the formulation and the stability of the liquid preparation. Further additives which can be employed in the present vaccine include, but are not limited to, dextrose, conventional antioxidants and conventional chelating agents such as ethylenediamine tetraacetic acid (EDTA). Parenteral dosage forms must also be sterilized prior to use.

EXAMPLES

Virus and Cells

The highly pneumovirulent strain of PRRSV, ATCC VR2385, was isolated from a pig exhibiting typical PRRS disease in the early 90's (Meng et al., 1996 (supra)). A comparative pathogenicity study using 9 different strains of type 2 PRRSV revealed that the VR2385 strain is highly pneumovirulent in cesarean-derived colostrum-deprived pigs (Halbur et al., 1996 (supra)). The virus stocks at passages 4 and 14 were used in this example. BHK-21 and MARC-145 cells were grown at 37° C. in Dulbecco's minimum essential medium (DMEM) supplemented with 10% FBS and antibiotics.

Determination of the Full-Length Genomic Sequence of VR2385 and Sequence Analyses:

The sequences of the ORFs 2 to 7 genes, but not ORF1, of the VR2385 isolate have been published (Meng et al., 1994). To determine the complete genomic sequence of VR2385, total RNAs were isolated from the passage 14 virus using TRI Reagen (MRC). Reverse transcription and cDNA synthesis were performed at 42° C. for 60 min in a 20-µl reaction mixture containing 100 U of Superscript II reverse transcriptase (Invitrogen), 10 mM deoxyribonucleoside triphosphate, 100 mM of DTT, 1 U of RNasin (Promega), and 0.5 µg of oligo dT primers (Invitrogen). The overlapping PCR fragments with approximately 2 kb in size for each fragment covering the entire genome of the VR2385 virus were amplified from the cDNA, and subsequently cloned into a pCR-2.1 vector (Invitrogen). Six individual clones of each fragment were selected for sequencing. The consensus sequences were assembled and used for sequence analysis utilizing the Lasergene software (Version 8, DNA STAR, Inc.).

Example 1

Construction of an Infectious cDNA Clone of a Highly Virulent Strain of North American PRRSV VR2385

Seven overlapping genomic fragments covering the entire viral genome of the strain VR2385 flanked by unique restriction enzyme sites were amplified by RT-PCR from MARC-145 cells infected by VR2385 strain (Meng, Paul, and Halbern, 1995 (supra)). Six clones of each fragment were sequenced, and the clone containing the consensus sequence was used for the assembly of the infectious clone. Each fragment was ligated stepwise into a low-copy-number plasmid pACYC177 between AscI and XbaI with a stuffer fragment containing unique restriction sites, resulting in the assembly of a full-length cDNA clone (FIG. 1). RNA transcripts from the full-length VR2385 clone are infectious when transfected into BHK cells (FIG. 2), and the rescued virus from BHK cells infects MARC-145 cells (FIG. 2), indicating that the VR2385 clone is infectious. This infectious clone therefore is critical in facilitating the DNA shuffling work in this study.

More specifically, after determining the sequence at the extreme 5'-end of the viral genome using the GeneRACER kit (Invitrogen), a total of 7 overlapping fragments (AB, BF, FS, SP, PS, SA, AN) with unique restriction enzyme sites that cover the entire viral genome were amplified from the cDNA of the passage 14 VR2385 virus stock. A T7 RNA polymerase core sequence was engineered immediately upstream of the 5'-end of the VR2385 genome in the fragment AB during the RT-PCR using primers T7ABf and ABr (FIG. 1; Table 1). A 20-poly(A) nucleotides were introduced immediately downstream of the 3'-end of the viral genome in the fragment AN. A total of 6 individual clones for each fragment were selected for sequencing, and the clone containing the consensus sequence was used for the assembly of the full-length cDNA clone. Primers mFSr and mSPf (SEQ ID No:9)(Table 1) were used to mutate a single nucleotide to generate a SphI restriction site in the fragments FS and SP for assembly. A low-copy number plasmid, pACYC177 (New England BioLab), was modified by replacing the fragment between the BamHI and BglI sites with a stuffer fragment to facilitate the cloning and assembly process (Fang et al., 2006). Each of the RT-PCR fragments was used to sequentially replace the stuffer with the same restriction enzyme sites on the modified vector pACYC-177, resulting in the assembly of a full-length cDNA clone of the VR2385 virus. The single nucleotide mutation introduced in the SP fragment was then changed back to the consensus sequence by using a site-directed mutagenesis kit (Invitrogen) with primers mutSphIf (SEQ ID No:16) and mutSphIr (SEQ ID No:17) (Table 1) after assembly of the fragments FS and SP to the backbone. This full-length cDNA clone of the passage 14 virus, which contains the 435-bp nsp2 deletion, was designated as pACYC-VR2385-CA.

Example 2

Development of an Improved DNA-Launched Reverse Genetics System for PRRSV

Figure 3A:
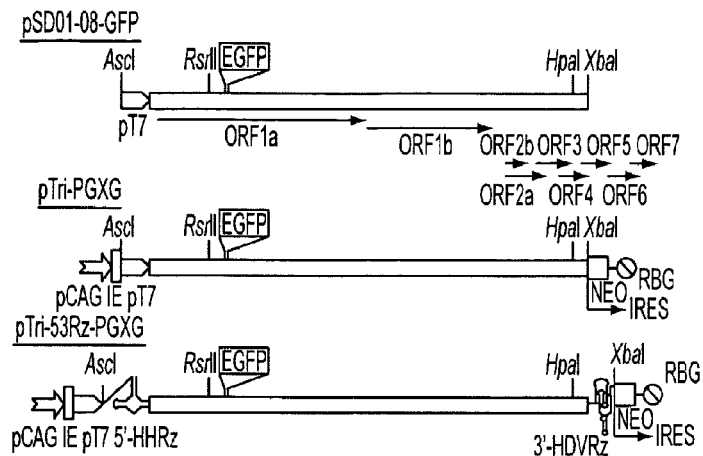
FIGS. 3(a)-(b) illustrate an exemplary DNA-launched PRRSV infectious clone.
Figure 3B:
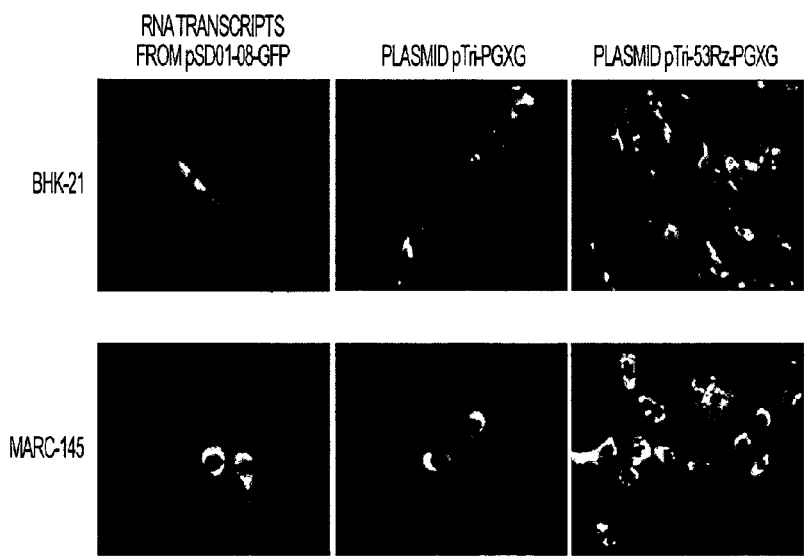

In order to facilitate DNA shuffling and subsequent recovery of shuffled chimeric viruses, the inventors of this invention developed an improved novel DNA-launched reverse genetics system for the European PRRSV genotype (strain pSD01-08) and North American genotype (strain VR2385), by introduction of ribozyme elements at both termini of the viral genomic cDNA that was placed under the control of a eukaryotic hybrid promoter (FIG. 3). The GFP reporter gene inserted in the nsp2 region was used to monitor the virus replication. It is demonstrated that the PRRSV rescue efficacy of the DNA-launched system was approximately 10- to 50-fold higher than the RNA-based system and the traditional DNA-launched system without the engineered ribozyme elements, as determined by reporter GFP level in transfected cells and peak titer of the recovered virus (FIG. 3) (Huang, et al, 2009 (supra)). The establishment of this improved DNA-launched reverse genetics system for PRRSV greatly facilitates the screening of shuffled chimeric viruses since the shuffled PRRSV genes can now be cloned in the DNA-launched clone and tested directly for infectivity by transfecting plasmid DNA into MARC-145 or BHK cells without having to first producing RNA transcripts, and the GFP marker in the nsp2 will serve as an indicator for selection of viable chimeric viruses after DNA shuffling.

Specifically, pACYC-VR2385-CA, is a DNA-launched infectious clone prepared essentially as described previously (Huang et al., 2009; Huang and Meng, 2010). A three-step subcloning procedure was performed to introduce the ribozyme elements and construct the final infectious clone. Briefly, A PCR fragment with the fusion of a hammerhead ribozyme (HHRz) to the 5'-end of the viral genome was cloned into pACYC-VR2385-CA by using the single restriction site BamHI. Next, a hepatitis delta virus ribozyme (HD-VRz) was engineered to the 3'-end using the same fragment-replacing strategy with the restriction sites AclI and XbaI. Subsequently, the fragment IR-XA from the vector pIRES-EGFP2 containing the CMV promoter (1987→5308, 0→619) was amplified using primers pIR-XbaIf (SEQ ID No:18) and pIR-AscIr (SEQ ID No:19) (Table 1), incorporating the unique restriction sites AscI and XbaI, which were then used to ligate this fragment upstream to the viral genome. The full-length viral genome engineered with HHRz and HDRz at both termini was released from the backbone vector pACYC-177 by double digestion with AscI and XbaI, and subsequently ligated to the PCR product IR-XA digested with the same restriction enzymes AscI and XbaI to produce the DNA-launched infectious clone pIR-VR2385-CA.

Example 3

Figure 4:
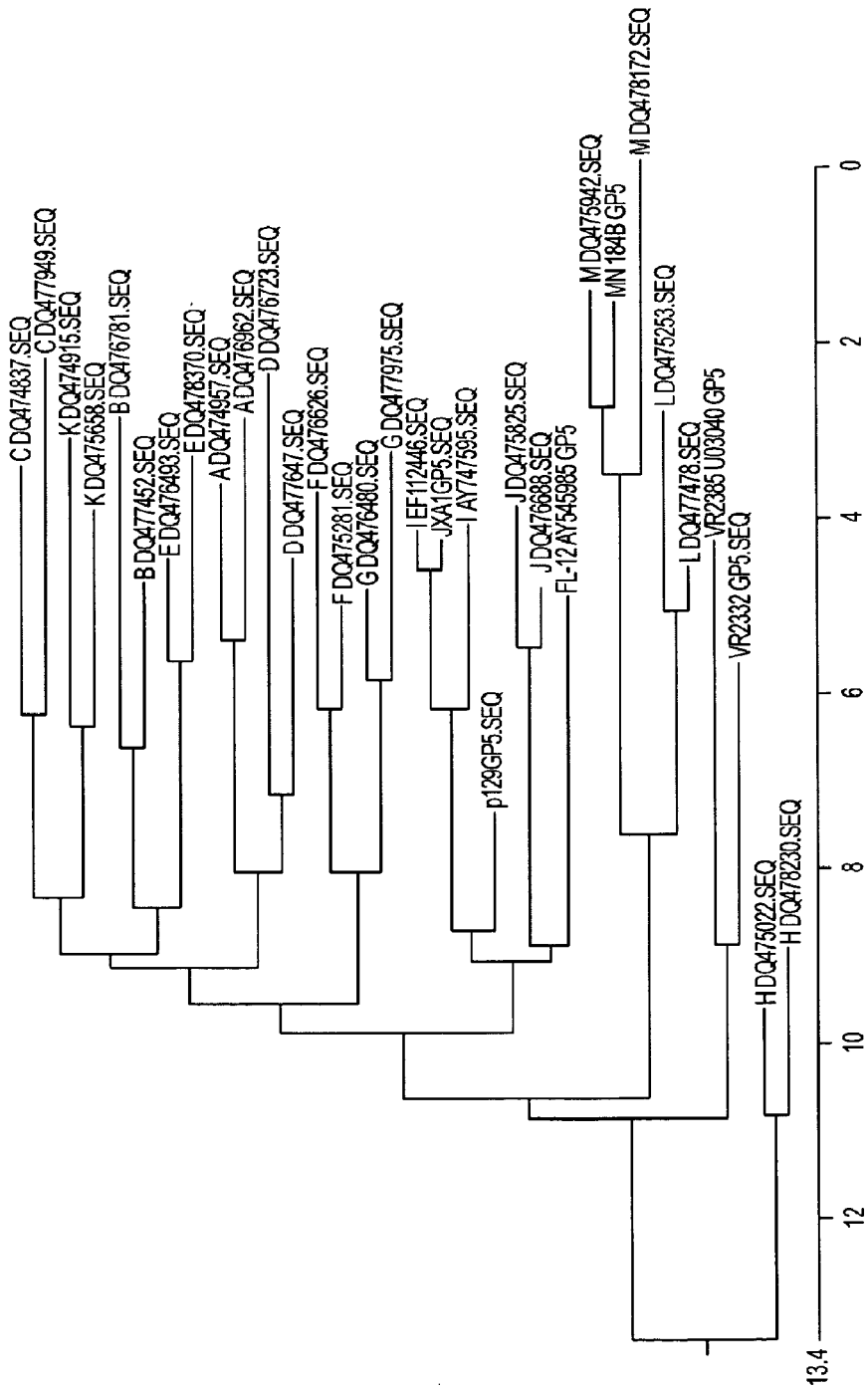
FIG. 4 illustrates five genetically distinct strains of PRRSV that are selected for the DNA shuffling based on an alignment of the representative strains of the nine major clusters of type 2 North American strains of PRRSV, i.e., strains VR2385, FL12, MN184, DQ474837 (C), and JXA1 from a pig high fever disease in China. (Shi M, Lam T T, Hon C C, Murtaugh M P, Davies P R, Hui R K, Li J, Wong L T, Yip C W, Jiang J W, Leung F C. Phylogeny-based evolutionary, demographical, and geographical dissection of North American type 2 porcine reproductive and respiratory syndrome viruses. J Virol. 2010 September; 84(17):8700-11).
Figure 5:
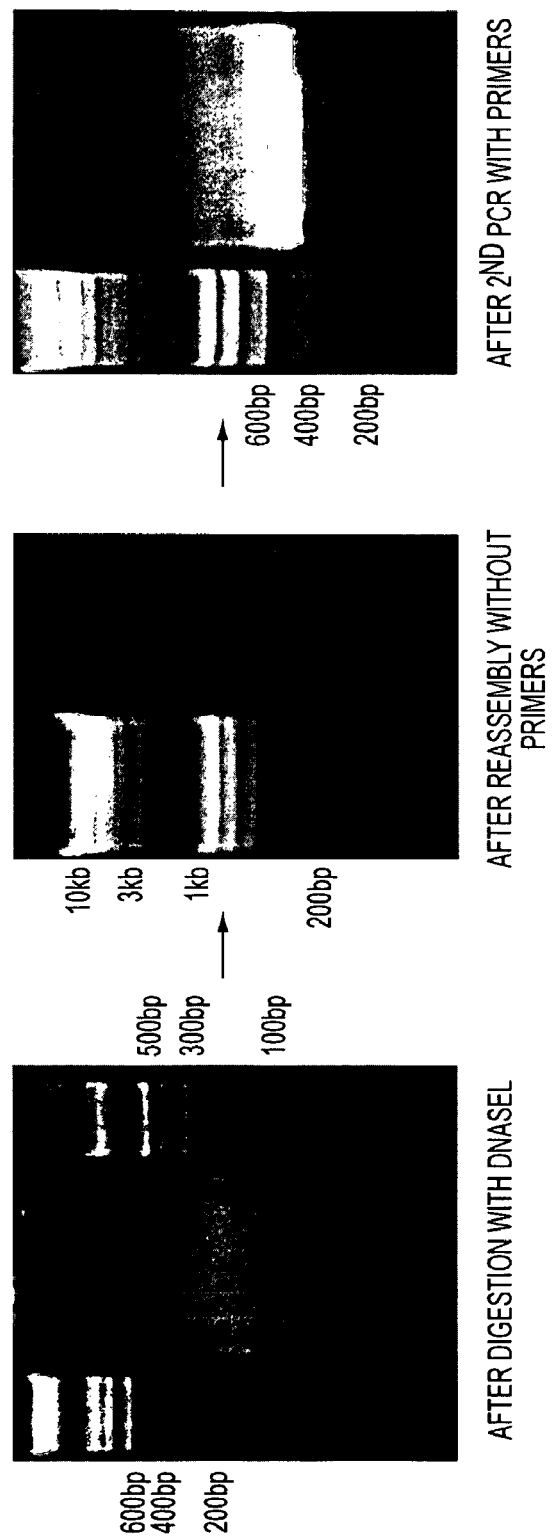
FIG. 5 shows representative DNA electrophoresis gel pictures during an exemplary DNA Shuffling process.

Molecular Breeding of the GP5 Gene from 5 Genetically Different Strains of PRRSV The GP5 is the most variable structural protein, with only about 51-55% amino acid identity between North American and European isolates. Five genetically different strains of North American genotype of PRRSV [strains VR2385, FL12, MN184, DQ474837 (C), and JXA1 from a pig high fever disease in China] were selected for DNA shuffling of the GP5 genes (FIG. 4), and these 5 strains represent 5 distinct clusters of North American isolates (FIG. 4). A 473-nt sequence excluding the 13-bp overlapping region between GP5 and M (to preserve the M gene start codon), the 21-nt junction sequence upstream the M gene, and the 93-nt signal peptide sequence at the 5' end of ORF5. The GP5 sequences from MN184B, DQ474837 (C) and JXA1 were synthesized based on the GenBank sequences and the GP5 sequences of VR2385 and FL12 were amplified from their infectious cDNA clones. The GP5 genes from different parental strains were mixed in equal molar in a 100-μl volume. The mixture was randomly fragmented by digestion with DNase I at 15° C. for 90 sec. The digestion reaction were terminated by adding 5-μl of 0.5M EDTA and heat-inactivated at 85° C. for 10 min. A smear of small fragments with sizes of about 50 bp to 150 bp were gel-purified (FIG. 5). The shuffled fragments were reassembled by PCR without primer using pfu polymerase, followed by a $2^{nd}$ PCR amplification with GP5 gene-specific primers (GP5trunc-F (SEQ ID No:29) and GP5trunc-R (SEQ ID No:30)) to generate an expected truncated GP5 product of 450 bp (FIG. 5).

Parental Strains Preparation.

The GP5 sequences with a size of 603 bp from the five selected genetically distinct strains of PRRSV were used as the substrates for DNA shuffling. The GP5 sequences of MN184B, DQ474837 and JXA1 were synthesized from GenScript USA Inc based on the corresponding sequence published in NCBI database and were subsequently amplified by PCR using specific primers, respectively (SEQ ID No:20-28) (Table 1). The other GP5 sequences were amplified from the infectious clones pIR-VR2385-CA and pFL12 (Truong et al., 2004).

Fragmentation with DNase I Digestion.

The five PCR products were mixed together equimolarly with a total amount of 5-μg and diluted to a 50-μl of 50 mM Tris.HCl, PH 7.4 and 10 mM $MgCl_2$. The mixture was incubated at 15° C. for 1 min with 0.15 U of DNaseI (15.32 U/μl Sigma). The digestion was terminated with adding 5 μl of 0.5M EDTA followed by 15-minute incubation at 85° C. for further inactivation. Fragments of 50-150 bp were purified from 2% agarose gels using Qiaquick gel extraction kit (Qiagen).

Reassembly of the Digested Fragments.

The purified fragments were added to the Pfu PCR mixture (10-fold diluted Pfu buffer, 0.4 mM each dNTP, 0.06 U Pfu polymerase from Stratagene) without primers. A PCR program (95° C. for 4 min; 35 cycles of 95° C. for 30 s, 60° C. for 30 s, 57° C. for 30 s, 54° C. for 30 s, 51° C. for 30 s, 48° C. for 30 s, 45° C. for 30 s, 42° C. for 30 s, 72° C. for 2 min; and final 72° C. for 7 min) was performed to reassemble the digested fragments. A 10-μl of the reaction mixture was loading on the agarose gel to determine the quality of the reassembled products.

PCR Amplification with Primers.

Primers GP5trunc-F (SEQ ID No:29) and GP5trunc-R (SEQ ID No:30) (Table 1) were used to amplify the shuffled products excluding the signal peptide sequence of ORF5 and the TRS plus the overlapping region of ORF6. The PCR mixture contained 5 μl of reassembled products, 0.2 μM of each primer, 430 of Platinum High Fidelity PCR SuperMix (Invitrogen). The PCR condition was set as: 4 min 95° C.; 25 cycles of 30 s 95° C., 30 s 55° C., 30 s 72° C.; final 7 min 72° C. A single band of correct size was detected and the shuffled GP5 was obtained after gel purification.

Fusion PCR with Shuffled Products.

To incorporate two restriction sites for cloning, three-fragment fusion PCR was performed. Two flanking fragments including the restriction sites AclI and XbaI were amplified from pIR-VR2385-CA, respectively, and fused to the shuffled GP5. A 1.8-kb fragment containing the shuffled GP5 was obtained after gel purification.

Cloning the Shuffled GP5 and Evaluating the Quality of DNA Shuffling.

The fusion products containing shuffled GP5 were digested with AclI and XbaI and subsequently ligated to the DNA launched backbone pIR-2385-CA to generate a mixture of shuffled clones. Ten individual clones were selected for sequencing of GP5 region. The sequences of the 10 clones were compared with the five parental PRRSV strains and the quality of shuffling was analyzed after alignment using MegAlign (Version 8, DNA STAR, Inc.).

Example 4

Rescue and Recovery of Shuffled Infectious Chimeric PRRSV Viruses

Figure 6:
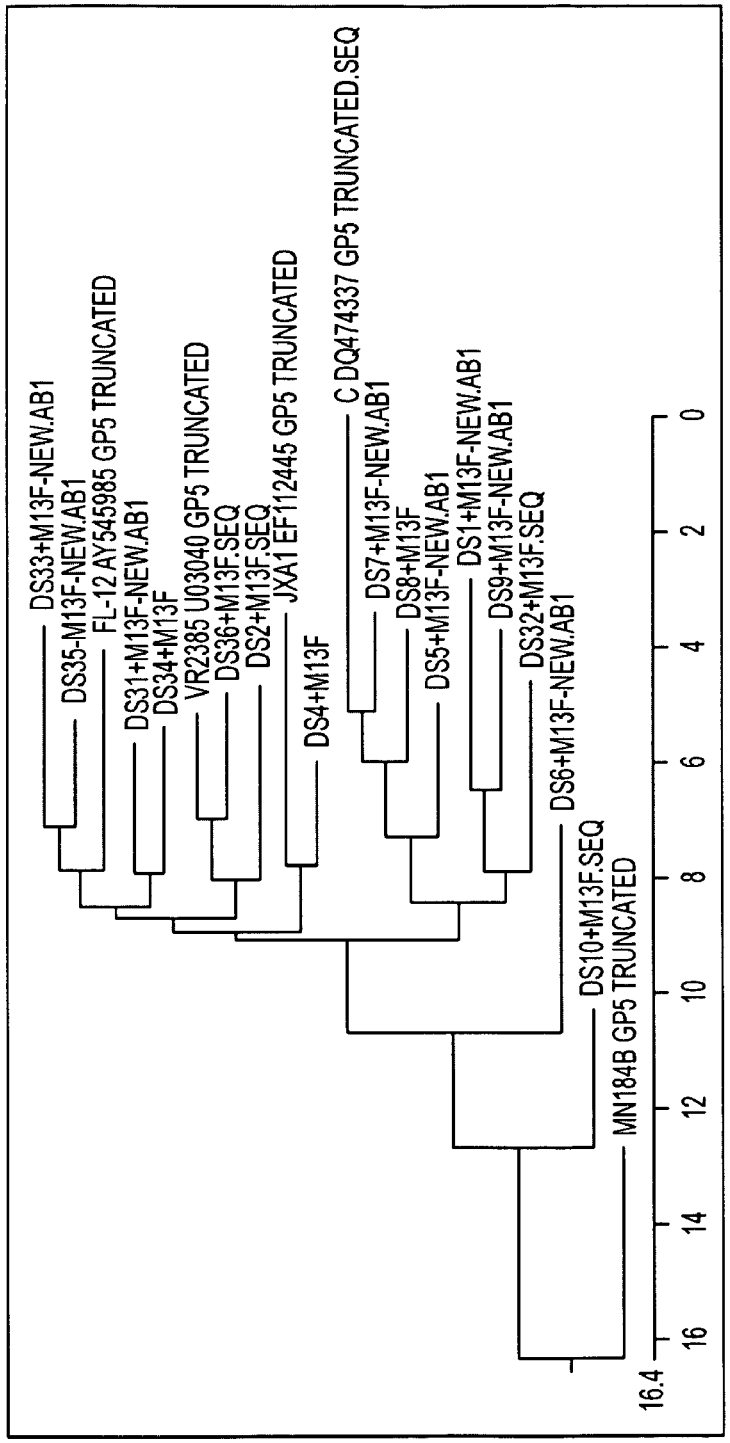
FIG. 6 is a phylogenetic alignment of the sequences of selected shuffled GP5 products, which were widely distributed containing partial parental sequences from all of the parental strains. The parental sequences were also included in the alignment.
Figure 7:
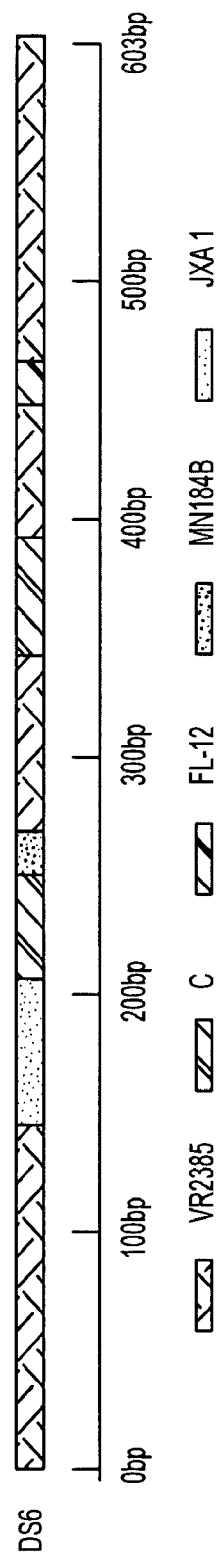
FIG. 7 illustrates the GP5 gene from a representative clone that contains chimeric sequences from all 5 parental strains. Each color represents the sequence for each parental strain: yellow (VR2385), orange (C: DQ474837), pink (FL-12), blue (MN184), green (JXA1).

The shuffled GP5 products were cloned into the backbone of the DNA-launched VR2385 infectious cDNA clone using two unique restriction enzyme sites, AclI and XbaI, which are generated by a fusion PCR with 2 flanking fragments. The shuffled products are sequenced to check the parental virus sequence contribution to the shuffled chimeric GP5 genes. The results showed the sequences of the selected shuffled GP5 products were widely distributed and contained parental sequences from the 5 distinct PRRSV strains (FIG. 6). A representative shuffled GP5 gene containing the sequences from all five parental strains was showed in FIG. 7.

Figure 8A:
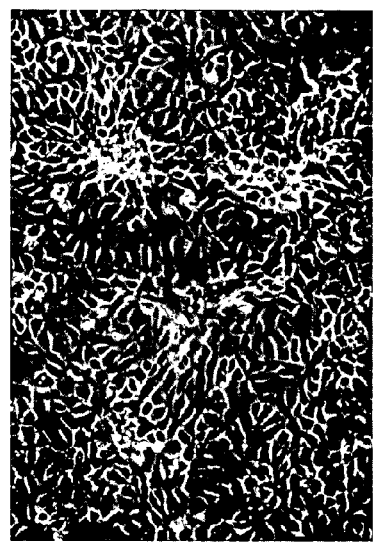
FIG. 8A exemplifies detection of chimeric viruses containing shuffled GP5 genes in BHK-21 cells transfected with VR2385 infectious cDNA clone with shuffled GP5 genes.
Figure 8B:
FIG. 8B demonstrates cytopathic effect (CPE) of MARC-145 cells infected with shuffled chimeric virus mixture at 2 days post-infection.
Figure 8C:
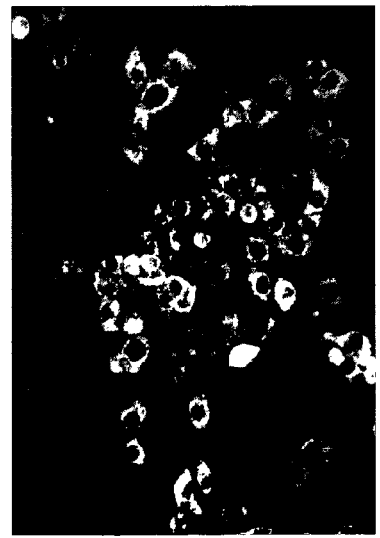
FIG. 8C illustrates detection of infectious chimeric viruses containing shuffled GP5 genes at 3 days post-infection of MARC-145 cells with the VR2385 infectious cDNA clone with shuffled chimeric GP5 gene.

The shuffled GP5 genes were subsequently cloned in the genomic backbone of the VR2385 infectious cDNA clone. The mixture of VR2385 cDNA clones containing shuffled GP5 genes was transfected into BHK-21 cells. IFA was performed 2 days post-transfection (FIG. 8A), and the supernatant was collected to infect MARC-145 cells. CPE was observed 2 days post-infection (FIG. 8B). 3 days post-infection, IFA was performed to detect the viable infectious chimeric virus (FIG. 8C).

Example 5

Screening of Viable Infectious Chimeric Viruses Containing the Shuffled GP5

In order to rescue of chimeric PRRSV containing the shuffled GP5 from the DNA-launched clones, BHK-21 cells at a 60% confluency in 6-well plates were transfected with 3 μg of the mixture of pIR-VR2385-CA-based GP5-shuffled clones using 8 μl of Lipofectamine LTX (Invitrogen) according to the manufacturer's instruction. At 48 h post-transfection, the supernatant from cultured cells was harvested and passaged onto MARC-145 cells. IFA was performed in transfected BHK-21 cells using the anti-PRRSV N monoclonal antibody (SDOW17) to confirm the replication of these shuffled viruses. The propagation of rescued virus was confirmed by IFA in MARC-145 cells at 72 h post-infection. The supernatant of infected cells was collected and used for secondary infection of MARC-145 cells to generate sufficient virus stocks for further plaque purification.

Confluent monolayers of MARC-145 cells cultured in individual wells of a 6-well plate were inoculated with serially-diluted shuffled viruses (1, $10^{-1}$, $10^{-2}$, $10^{-3}$) respectively. After 1 h incubation, the inoculum was removed and 1% agarose overlay was applied to the monolayer. Plaques were stained with neutral red solution (Sigma) 4 days post-infection at 37° C. Six individual plaques were picked up by a P200 pipette with sterile filtered tips and re-suspend in 500 μl PBS the next day. The plaques representing six purified PRRSV shuffled viruses were further propagated in MARC-145 cells to make virus stocks, respectively. Viral RNA was extracted from the each purified virus and sequences of the GP5 region were determined by RT-PCR.

Example 6

Figure 9:
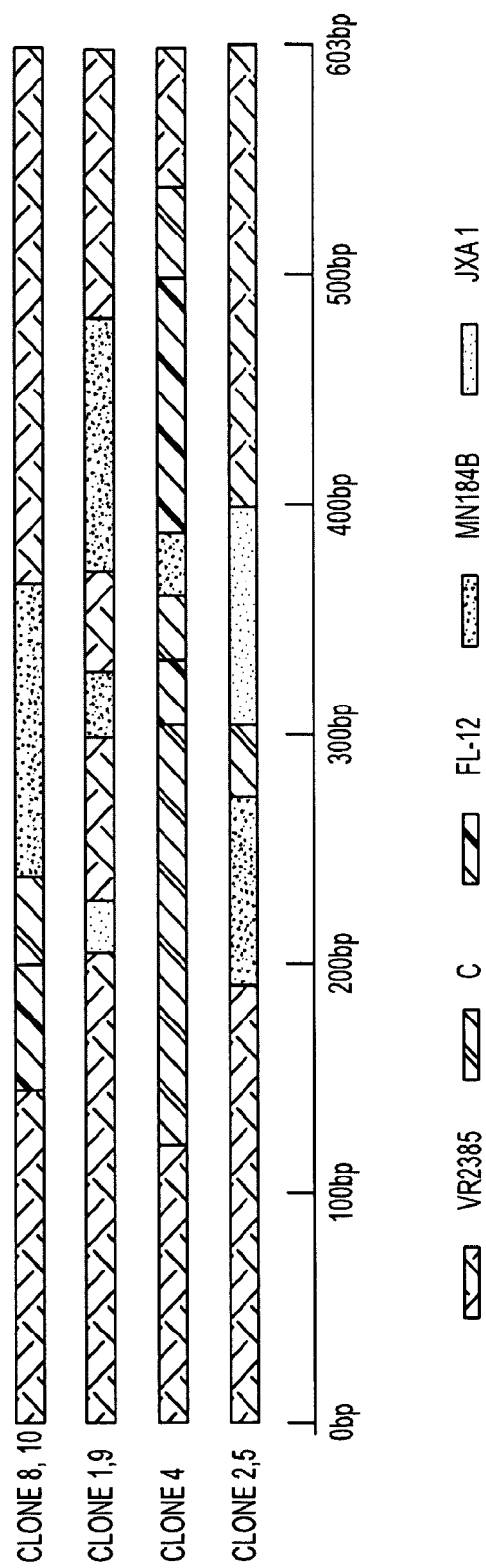
FIG. 9 illustrates subcloning the RT-PCR products into the pCR-Blunt-end vector for sequencing confirmation of the rescued chimeric viruses.

Sequencing Confirmation of the Rescued Infectious Chimeric Viruses Contain Sequences from all 5 Parental Strains of PRRSV Supernatant from infected cells was collected, and used for plaque purification. A total of 6 plaque-purified viruses selected from the plaque assay were cloned to pCR-Blunt vector and subsequently sequenced, and the viruses containing the chimeric GP5 sequences from all 5 parental strains were confirmed by sequencing (FIG. 9). The recovered chimeric viruses contained the parental sequences of the 5 strains of PRRSV (FIG. 9). The results indicated that we have successfully generated infectious chimeric viruses containing sequences of the 5 parental strains of PRRSV by DNA shuffling, and these infectious chimeric viruses will be the candidates for further development into a modified live-attenuated vaccine.

The results in this invention here demonstrated the utility of the molecular breeding and DNA shuffling for creating novel chimeric PRRSV as a novel MLV. The chimeric MLV produced in this study will confer broad protection against heterologous strains of PRRSV. The rescued chimeric viruses with the shuffled GP5 genes can also serve as the backbone to incorporate additional shuffled genes such as GP2, GP3, GP4, M, or other non-structural viral proteins to produce even more broadly representative chimeric viruses as vaccine candidates. In addition, the shuffled chimeric GP5 gene along with shuffled chimeric M, GP2, GP3 and GP4 will be excellent candidates for subunit chimeric protein vaccines against PRRSV as well.

TABLE 1

Oligonucleotide primers used in this study

| Primer ID | Sequence (5' > 3') | nt position in VR2385-CA virus genome |
|---|---|---|
| Fragment AB | | |
| ABf (SEQ ID No: 1) | ATGACGTATAGGTGTTGGCTCT | 1-22 |
| ABr (SEQ ID No: 2) | GGGCTCAACCCTTATTCTA | 1255-1273 |
| T7ABf (SEQ ID No: 3) | TTGGATCCGGCGCGCCTAATACGACTCACTATAGG ATGACGTATAGGTGTT | 1-16 |
| Fragment BF | | |
| BFf (SEQ ID No: 4) | CCCAAATGGACCTATCGT | 1150-1167 |
| BFr (SEQ ID No: 5) | TCAGAGGGTTGCTCAATGGG | 4118-4137 |
| Fragment FS | | |
| FSf (SEQ ID No: 6) | GACCTGTGTGATCGGTTTTGCG | 4031-4052 |
| mFSr (SEQ ID No: 7) | GTCAAGGGCAGGGTAAGGGCAT | 4680-4701 |
| Fragment SP | | |
| SPr (SEQ ID No: 8) | TGGCGGCTAGCAGTTTAAACAC | 7252-7273 |
| mSPf (SEQ ID No: 9) | AGCATGCCCTTACCCTGCCCTT | 4677-4698 |
| Fragment PS | | |
| PSf (SEQ ID No: 10) | GCCTGACTAAGGAGCAGTGTTT | 7236-7257 |
| PSr (SEQ ID No: 11) | TTGGGGAGCGGAGAGCTCGA | 10510-10529 |
| Fragment SA | | |
| SAf (SEQ ID No: 12) | CTGATCTAGAAGGGTCGAGCTC | 10496-10517 |
| SAr (SEQ ID No: 13) | TGGTCAACTACCAAGGAACGTT | 13234-13255 |
| Fragment AN | | |
| ANf (SEQ ID No: 14) | GTCAAGGAATTTACCCAACGTT | 13218-13239 |
| ANrpolyA (SEQ ID No: 15) | TACATATGTTTTTTTTTTTTTTTTTTTTT TAATTTCGGCC | 14968-14977 |
| For site-directed point mutation | | |
| mutSphl-f (SEQ ID No: 16) | CATTTCCCAGCATGGCCTTACCCTGCCCTTG | 4669-4699 |
| mutSphl-r (SEQ ID No: 17) | CAAGGGCAGGGTAAGGCCATGCTGGGAAATG | 4669-4699 |
| For the construction of DNA-launched infectious clones | | |
| pIR-XbaIf (SEQ ID No: 18) | GCTCTAGAGCATAATCAGCCATACCACATTTGTAGAGG | |
| pIR-AscIr (SEQ ID No: 19) | GAAGGCGCGCCTCGAGATCTGAGTCCGGTAG | |
| For DNA shuffling of GP5 | | |
| JXA1f (SEQ ID No: 20) | ATGTTGGGGAAGTGCTTGACCG* | |
| JXA1r (SEQ ID No: 21) | CTAGAGACGACCCCATAGTTCCGCT* | |
| CMNf (SEQ ID No: 22) | ATGTTGGGGAAATGCTTGACCG* | |
| Cr (SEQ ID No: 23) | TTAAGGAAGACCCCATTGTTCCGC* | |

TABLE 1-continued

Oligonucleotide primers used in this study

| Primer ID | Sequence (5' > 3') | nt position in VR2385-CA virus genome |
|---|---|---|
| MNr (SEQ ID No: 24) | CTAAGGACGACCCC<u>ATT</u>GTTCCG | |
| FL12f (SEQ ID No: 25) | CTGGCAATTTGAATGTTCAAGT<u>ATG</u>* | |
| FL12r (SEQ ID No: 26) | CTAAAGACGACCCC<u>ATT</u>GTTCC* | |
| VR2385f (SEQ ID No: 27) | <u>ATG</u>TTGGGGAAATGCTTGACCG* | |
| VR2385r (SEQ ID No: 28) | CTAAGGACGACTCC<u>ATT</u>GTTCCG* | |
| GP5trunc-F (SEQ ID No: 29) | GGGAACAGCGGCTCAAATTTACAG | |
| GP5trunc-R (SEQ ID No: 30) | AGGGGTAGCCGCGGAACCAT | |

*: underline nucleotides represent start codon or stop codon of ORFS from different strains.

What is claimed is:

1. An infectious chimeric PRRSV comprising proteins that are chimeric of a plurality of genetically distinct strains, wherein the chimeric proteins are GP2, GP3, GP4, GP5, and M.

2. The infectious chimeric PRRSV set forth in claim 1, wherein the proteins are chimeric from at least two of genetically distinct strains.

3. The infectious chimeric PRRSV set forth in claim 2, wherein the at least two of genetically distinct strains comprising at least two of strains VR2385, FL12, MN184, DQ474837 (C), and JXA1.

4. The infectious chimeric PRRSV set forth in claim 1, wherein the chimeric proteins are produced via DNA shuffling.

5. An avirulent infectious chimeric PRRSV derived from chimeric PRRSV according to claim 1.

6. An inactivated chimeric PRRSV derived from chimeric PRRSV according to claim 1.

7. A modified live PRRSV vaccine derived from chimeric PRRSV according to claim 1.

8. The vaccine according to claim 7, further comprising an adjuvant.

9. The vaccine according to claim 7, wherein the vaccine protects against PRRSV infection.

10. A method of immunizing a pig against PRRSV viral infection, comprising administering to a pig an immunologically effective amount of the vaccine according to claim 7.

11. The method according to claim 10, comprising administering the vaccine parenterally, intranasally, intradermally, or transdermally to the pig.

12. The method according to claim 10, comprising administering the vaccine intralymphoidly or intramuscularly to the pig.

13. A method of protecting a pig against porcine reproductive and respiratory syndrome, comprising administering to a pig an immunologically effective amount of the vaccine according to claim 7.

14. A method for producing an infectious chimeric PRRSV, wherein the infectious chimeric PRRSV comprises proteins that are chimeric of a plurality of genetically distinct strains, wherein the chimeric proteins are GP2, GP3, GP4, GP5 and M, comprising:
mixing deoxyribonucleic acid molecules derived from a plurality of various genetically distinct strains of PRRSV encoding GP2, GP3, GP4, GP5 and M;
digesting the deoxyribonucleic acid molecules by using a nonspecific deoxy nuclease;
extending the digested deoxyribonucleic acid molecules via polymerase chain reaction without adding primer;
amplifying chimeric deoxyribonucleic acid molecules encoding GP2, GP3, GP4, GP5 and M;
inserting the amplified chimeric deoxyribonucleic acid molecules into an infectious deoxyribonucleic acid clone of PRRSV; and
infecting a host cell with the infectious deoxyribonucleic acid clone of PRRSV.

15. The method for producing infectious chimeric PRRSV viruses according to claim 14, wherein the infectious deoxyribonucleic acid clone of PRRSV comprising a first ribozyme at the 5' end of a complimentary sequence of PRRSV genome and a second ribozyme at the 3' end of the complimentary sequence of PRRSV genome.

16. The method for producing infectious chimeric PRRSV viruses according to claim 15, wherein the complimentary sequence of PRRSV genome is under the control of a eukaryotic promoter.

* * * * *